United States Patent
Marsh

(10) Patent No.: US 11,331,618 B2
(45) Date of Patent: May 17, 2022

(54) R2R MICROELECTROMECHANICAL GAS CONCENTRATOR

(71) Applicant: Encite LLC, Burlington, MA (US)

(72) Inventor: Stephen Alan Marsh, Carlisle, MA (US)

(73) Assignee: Encite LLC, Burlington, MA (US)

( * ) Notice: Subject to any disclaimer, the term of this patent is extended or adjusted under 35 U.S.C. 154(b) by 421 days.

(21) Appl. No.: 16/285,371

(22) Filed: Feb. 26, 2019

(65) Prior Publication Data

US 2019/0275458 A1 Sep. 12, 2019

Related U.S. Application Data

(60) Provisional application No. 62/639,522, filed on Mar. 7, 2018.

(51) Int. Cl.
*B01D 53/053* (2006.01)
*F04B 53/10* (2006.01)
(Continued)

(52) U.S. Cl.
CPC ....... *B01D 53/0446* (2013.01); *A61M 16/101* (2014.02); *B01D 53/047* (2013.01);
(Continued)

(58) Field of Classification Search
CPC .. B01D 53/0446; B01D 53/047; B01D 53/04; B01D 53/0473; B01D 53/0476; B01D 2253/108; B01D 2256/10; B01D 2256/12; B01D 2259/40003; B01D 2259/40007; B01D 2259/402; F04B 19/006; F04B 30/10; F04B 41/02; F04B 41/06; F04B 7/00; F16K 99/0003; F16K 99/0015; F16K 99/0051; F16K 2099/008; F16K 2099/0074; A61M 16/101
(Continued)

(56) References Cited

U.S. PATENT DOCUMENTS

| | | | | |
|---|---|---|---|---|
| 4,539,019 A | * | 9/1985 | Koch ................. | B01D 53/0476 95/19 |
| 5,441,597 A | * | 8/1995 | Bonne ................. | F15B 13/0405 216/17 |

(Continued)

FOREIGN PATENT DOCUMENTS

EP 1 426 094 6/2004

OTHER PUBLICATIONS http://www.murata-ps.com/emena/2012-05-22.html 2 pages.
(Continued)

*Primary Examiner* — Frank M Lawrence, Jr.
(74) *Attorney, Agent, or Firm* — Fish & Richardson P.C.

(57) ABSTRACT

Disclosed are techniques such as roll to roll processing to produce membrane valves in microelectromechanical systems that are integrated with micro-pumps that include a pump body having compartmentalized pump chambers. One application of this technology is as a valve assembly for a gas concentrator that includes a first micro pump for feeding an input gas stream, a second micro pump to supplying a vacuum and at least one sieve bed having a zeolite. The gas concentrator uses the valve assembly for controlling entry of gas from the first micro pump into the sieve bed and the second micro pump to vent.

25 Claims, 20 Drawing Sheets

(51) Int. Cl.
  *B01D 53/04* (2006.01)
  *B01D 53/047* (2006.01)
  *F16K 99/00* (2006.01)
  *A61M 16/10* (2006.01)

(52) U.S. Cl.
  CPC ..... *B01D 53/0473* (2013.01); *B01D 53/0476* (2013.01); *F16K 99/0003* (2013.01); *B01D 2253/108* (2013.01); *B01D 2256/10* (2013.01); *B01D 2256/12* (2013.01); *B01D 2259/402* (2013.01); *B01D 2259/40003* (2013.01); *B01D 2259/40007* (2013.01)

(58) Field of Classification Search
  USPC .......................................... 96/109–114, 121
  See application file for complete search history.

(56) References Cited

U.S. PATENT DOCUMENTS

| | | | |
|---|---|---|---|
| 5,687,767 A | 11/1997 | Bowers | |
| 5,827,358 A * | 10/1998 | Kulish | B01D 53/0473 96/115 |
| 5,836,750 A | 11/1998 | Cabuz | |
| 6,106,245 A | 8/2000 | Cabuz | |
| 6,168,395 B1 | 1/2001 | Quenzer et al. | |
| 6,179,586 B1 | 1/2001 | Herb | |
| 6,247,908 B1 | 6/2001 | Shinohara | |
| 6,261,066 B1 | 7/2001 | Linnemann | |
| 6,443,154 B1 | 9/2002 | Jalde | |
| 6,568,286 B1 | 5/2003 | Cabuz | |
| 6,758,107 B2 | 7/2004 | Cabuz | |
| 6,889,567 B2 | 5/2005 | Cabuz | |
| 7,090,471 B2 | 8/2006 | Xie et al. | |
| 7,802,970 B2 | 9/2010 | Singhal et al. | |
| 9,067,174 B2 * | 6/2015 | Daniels, Jr. | B01D 53/30 |
| 9,592,469 B2 | 3/2017 | Klee et al. | |
| 9,873,078 B2 | 1/2018 | Koerber et al. | |
| 2002/0029814 A1 | 3/2002 | Unger | |
| 2002/0117643 A1 * | 8/2002 | Winger | F15C 5/00 251/129.06 |
| 2003/0106799 A1 | 6/2003 | Covington et al. | |
| 2003/0231967 A1 | 12/2003 | Najafi et al. | |
| 2004/0103899 A1 | 6/2004 | Noble | |
| 2004/0115068 A1 | 6/2004 | Hansen et al. | |
| 2006/0230931 A1 * | 10/2006 | Bliss | B01D 53/053 95/130 |
| 2007/0059494 A1 | 3/2007 | Unger et al. | |
| 2009/0074595 A1 | 3/2009 | Chen et al. | |
| 2009/0129952 A1 | 5/2009 | Patrascu et al. | |
| 2009/0130607 A1 | 5/2009 | Slafer | |
| 2010/0181871 A1 | 7/2010 | Daniel et al. | |
| 2011/0207328 A1 | 8/2011 | Speakman | |
| 2013/0333564 A1 * | 12/2013 | Shelnutt | F04B 19/006 95/90 |
| 2014/0147346 A1 | 5/2014 | Chitnis et al. | |
| 2015/0231550 A1 * | 8/2015 | Morita | B01D 53/0446 96/110 |
| 2016/0131126 A1 | 5/2016 | Marsh | |

OTHER PUBLICATIONS

International Search Report and Written Opinion, PCT/US19/19738, dated Apr. 23, 2019, p. 1-17.

Nelsimar Vandelli et al.: "Development of a MEMS Microvalve Array for Fluid Flow Control," *Journal of Microelectromechanical Systems*, vol. 7, No. 4, Dec. 1, 1998, p. 1-9.

European Search Report, EP 19 765 002.1, dated Oct. 27, 2021, p. 1-11.

* cited by examiner

R2R MICROELECTROMECHANICAL GAS CONCENTRATOR

CLAIM OF PRIORITY UNDER 35 U.S.C. § 119

This application claims priority under 35 U.S.C. § 119 to U.S. Provisional Patent Application Ser. No. 62/639,522, filed Mar. 7, 2018, and entitled "R2R Microelectromechanical Gas Concentrator", the entire contents of which is incorporated herein by reference.

BACKGROUND

This specification relates to gas concentrators.

Gas concentrators such as oxygen concentrators are well-known. Gas concentrators are used in a variety of industrial and medical applications. Several different technological approaches or processes are known.

One process used in fabrication of gas concentrators, especially for medical applications is pressure swing adsorption (PSA). PSA uses the adsorption principal of gases being attracted and thus adsorbed by solid surfaces when such gases are under high pressure. At higher and higher pressures more gas is adsorbed, whereas as pressure is reduced gases adsorbed by a solid surface are desorbed (released). PSA is used to separate gases in a mixture of gases according to the attraction of the different gases to different solid surfaces.

A typical PSA based oxygen concentrator uses a molecular sieve supporting zeolite minerals to adsorb atmospheric nitrogen from an input gas stream, e.g., ambient air, and subsequently vent the nitrogen, effectively scrubbing nitrogen leaving other atmospheric gases to pass through. This leaves oxygen as the primary gas remaining.

A PSA-based oxygen concentrator includes an air compressor, two cylinders filled with zeolite pellets, a pressure equalizing reservoir, and valves and tubes. In a first half-cycle a first cylinder receives air from the compressor, as the pressure in the first cylinder rises from atmospheric to about 2.5 times normal atmospheric pressure (typically 20 psi/138 kPa gauge, or 2.36 atmospheres absolute) the zeolite becomes saturated with nitrogen. As the first cylinder reaches near pure oxygen (excluding small amounts of other minor atmospheric components) in the first half-cycle, a valve opens and the oxygen-enriched gas flows to the pressure equalizing reservoir that connects to a patient's oxygen hose. At the end of the first half of the cycle, there is another valve position change so that the air from the compressor is directed to the second cylinder. The pressure in the first cylinder drops as the enriched oxygen moves into the reservoir, allowing the nitrogen to be desorbed back into gas. Partway through the second half of the cycle, there is another valve position change to vent the gas in the first cylinder back into the ambient atmosphere, keeping the concentration of oxygen in the pressure equalizing reservoir from falling below about 90%. The pressure in the hose delivering oxygen from the equalizing reservoir is kept steady by a pressure reducing valve.

Another process used in fabrication of gas concentrators, especially for industrial applications is vacuum swing adsorption (VSA). The VSA process is especially used in those industrial processes that require higher pressures and flows than medical units. The VSA process uses adsorbents, e.g., zeolites, for the target gas, e.g., nitrogen, a single low-pressure blower for a first phase and a valve that reverses the flow through the blower so that a second, e.g., regeneration phase occurs under a vacuum by purging the gas adsorbed. The purged gas is recycled and partially used as feed gas in the first step. Using two adsorbent vessels allows near-continuous production of the target gas and also permits pressure equalization, where the gas leaving a first vessel being depressurized is used to partially pressurize the second vessel.

Another process is vacuum pressure swing adsorption (VPSA). The VPSA process applies pressurized gas to the (VSA) separation process and also applies a vacuum to the purge gas (VSA) process. The VPSA process is among the most efficient gas concentration process.

Another process is rapid pressure swing adsorption (RPSA). Rapid pressure swing adsorption or RPSA is frequently used in portable oxygen concentrators. Building on VSA, RPSA works by quickly cycling the pressure in a vessel in the first phase of VSA while alternately venting opposite end of the vessel at the same rate. This means that un-adsorbed gases progress along the vessel faster than adsorbed gases and are vented at the distal end, while adsorbed gases do not get the chance to progress and are vented at the proximal end.

Portable gas concentrators such as oxygen concentrators are also well-known. However, in the case of known portable oxygen concentrators the term portable is relative. By portable is meant a device that is carried on a user's shoulder or wheeled behind a user or affixed to a wheelchair. The "portable" aspect of known portable oxygen concentrators are that they can be transported, as known portable oxygen concentrators tend to be relatively large, heavy and expensive.

SUMMARY

According to an aspect a gas concentrator, includes a micro pump, a sieve bed having an input and an output, and a valve assembly for controlling entry of a multi-component gas from the micro pump into the input to the sieve bed, venting of a first component of the gas, and feeding a concentrated second component of the gas from the output of the sieve bed to an outlet port of the gas concentrator.

This aspect can include one or more of the following:

The valve assembly includes plural valves disposed on a common substrate layer, with the plural valves interconnected among inlets and outlets of the valves, via passages disposed in the common substrate layer. The micro pump, the sieve bed and the valve assembly provide a first channel, the sieve bed is a first sieve bed having an input port and an output port, and the gas concentrator further includes a second channel including a second sieve bed having an input coupled via the valve assembly to the micro pump, and the second sieve bed having an output, and an equalization valve coupled between the second ports of the first and second sieve beds.

At least some of the plural valves are membrane valves. At least some of the membrane valves include a body having a chamber with first and second ports through the body that define a passage through the body and a pair of spaced membranes each carrying an electrode, the membranes affixed to walls of the body and disposed in the chamber, with the membranes responsive to electrical signals applied to the electrodes, with like charges applied to the electrodes to cause the membranes to flex away from each other to open the passage and with opposite charges applied to the electrodes to cause the membranes to flex towards each other to close the passage.

The valve assembly includes an input valve having an input port coupled to the micro pump and an output port coupled to a first port of the sieve bed, the input valve controlled by an input signal to selectively open and close the input valve, a purge valve having an input port coupled to a second port of the sieve bed controlled by a purge signal to selectively open and close the purge valve, a vent valve having an input port coupled to the first port of the sieve bed and an output coupled to a vent output of the gas concentrator, the vent valve controlled by a vent signal to selectively open and close the vent valve, and an output valve having an input port coupled to the second port of the sieve bed and an output port coupled to the output of the gas concentrator, the output valve controlled by an output signal to selectively open and close the output valve.

The micro pump, the sieve bed and the valve assembly provide a first channel, and the gas concentrator further includes a second channel including a second sieve bed coupled to the valve assembly. The input, purge, vent and output valves and signals are first valves and first signals, and the valve assembly further comprises for the second channel, a second input valve having an input port coupled to the micro pump and an output port coupled to a first port of the second sieve bed, the second input valve controlled by a complement of the first signal to selectively open and close the second input valve; a second purge valve having an input port coupled to a second port of the sieve bed controlled by a second purge signal to selectively open and close the second purge valve; a second vent valve having an input port coupled to the first port of the sieve bed and an output coupled to the vent output of the gas concentrator, the second vent valve controlled by a second vent signal to selectively open and close the vent valve, an equalization valve coupled between the second ports of the first and second sieve beds, and an output valve having an input port coupled to the second port of the second sieve bed and an output port coupled to the output of the gas concentrator, the output valve controlled by a second output signal to selectively open and close the output valve.

The micro pump is a first micro pump and the sieve bed is a first sieve bed, with the gas concentrator further including a second sieve bed having a first port coupled to the valve assembly and a second micro pump coupled to a vent port of the valve assembly. The first and second sieve beds have second ports and the valve assembly further includes an equalization valve coupled between the second ports of the first and second sieve beds. The gas concentrator further includes an output gas reservoir coupled to an output of the valve assembly. The valve assembly is further configured to purge gas from the sieve bed and the gas concentrator further includes an purge gas reservoir coupled to a purge output port of the valve assembly. The gas concentrator further includes electronic circuitry including timing generator circuitry having output signal lines coupled to electrodes on the valves to provide timing signals to valves in the valve assembly. The electronic circuitry further includes a waveform generator that produces the signals having either a positive charge or a negative charge relative to a ground potential.

According to an additional aspect, a method of manufacturing a gas concentrator includes forming a valve assembly by patterning a body layer of material to form plural, interconnected compartments, laminating a first sheet of a flexible material carrying a first conductive layer over a first surface of the body layer, and laminating a second sheet of a flexible material carrying a second conductive layer over a second opposing surface of the body layer to provide the valve assembly, coupling the valve assembly to a first micro pump that provides input gas to the gas concentrator and to a second micro pump that provides venting of a component of the input gas, and coupling the valve assembly to a first sieve bed and a second sieve bed with each including a zeolite to adsorb a first gas from the input gas stream.

This aspect can include one or more of the following:

The body layer is a first body layer, the method further includes patterning second and third body layers to provide a first end cap compartment and a second end cap compartment, and stacking the first end cap compartment over the first surface of the composite laminated structure and the second end cap compartment over the second surface of the composite laminated structure.

Patterning the body layer includes patterning the body to form the plural compartments for the first channel and the second channels with each of the compartments correspond to a valve in the valve assembly, and with the first channel and the second channel each including an input valve, a vent valve, a purge valve and an output valve.

According to an additional aspect, a valve, includes a body having a chamber with first and second ports through the body that define a passage through the body, and a pair of spaced membranes each carrying an electrode, the membranes affixed to walls of the body and disposed in the chamber, with the membranes configured upon application of charges to the electrodes to attract to each other to close the passage through the chamber in a first mode and to repel each other to open the passage through the chamber in a second mode.

This aspect can include one or more of the following:

The valve further includes a first end cap compartment, and a second end cap compartment, with the first end cap compartment over the first surface of the composite laminated structure and the second end cap compartment over the second surface of the composite laminated structure.

The valve further includes electronic circuitry including timing generator circuitry having output signal lines coupled to electrodes to control operation of the valve.

The body and pair of spaced membranes are a first body and a first pair provide a first valve element, the valve further including a second valve element, including a second body having a chamber with first and second ports through the second body that define a passage through the second body, and a second pair of spaced membranes each carrying an electrode, the membranes affixed to walls of the body and disposed in the chamber of the second body, with the membranes configured upon application of charges to the electrodes to attract to each other to close the passage through the chamber in a first mode and to repel each other to open the passage through the chamber in a second mode, and a unit compartment that is coupled in series in between an output of the first valve element and an input of the second valve element.

The valve further includes electronic circuitry including timing generator circuitry having output signal lines coupled to electrodes to control operation of the valve, according to a sequence that: opens the first valve element while the second valve element is closed to allow gas to enter through the first valve element and into the unit compartment, equilibrates gas pressure in the first valve element and unit compartment, closes the first valve element, and opens the second valve element to allow gas in the unit compartment to enter the second valve element and flow out of the valve.

One or more of the above aspects may have one or more of the following advantages.

The weight of gas concentrators most likely would be relatively light in comparison with current commercially available oxygen concentrators. The overall size would be comparatively small in comparison with current commercially available oxygen concentrators and most likely driven by sieve bed and/or battery size. The cost would be relatively inexpensive in comparison with commercially available oxygen concentrators. For a given output requirement, the size of the sieve beds can be reduce by active separation and regeneration processes, pressure and vacuum pumps.

The details of one or more embodiments of the invention are set forth in the accompanying drawings and the description below. Other features, objects, and advantages of the invention are apparent from the description and drawings, and from the claims.

DETAILED DESCRIPTION

Overview

Microelectromechanical systems such as micro-sensors, micro CPAP (continuous positive air pressure) devices, and micro pumps can be constructed as discussed in my co-pending patent applications US-2015-0267695-A1, filed Sep. 24, 2015; US-2016-0131126-A1, filed May 12, 2016; US-2018-0015247-A1, filed Jan. 18, 2018; US-2018-0038754-A1, filed Feb. 8, 2018, all of which are incorporated herein by reference in their entireties. In particular these devices can be constructed by roll to roll (R2R) microelectromechanical systems processing (MEMS) or (R2R MEMS) processing.

Gas Concentrators

Gas concentrators such as oxygen concentrators that employ micro pumps and membrane valves and especially ones fabricated by roll to roll microelectromechanical systems processing (R2R MEMS) will now be described. Gas concentrators typically take a multi-component input gas mixture, e.g., ambient air, and extract one or more gas components, e.g., nitrogen from the gas mixture, which component is subsequently vented to concentrate, a remaining component(s), e.g., oxygen in a gas output from the gas concentrator.

Figure 1:
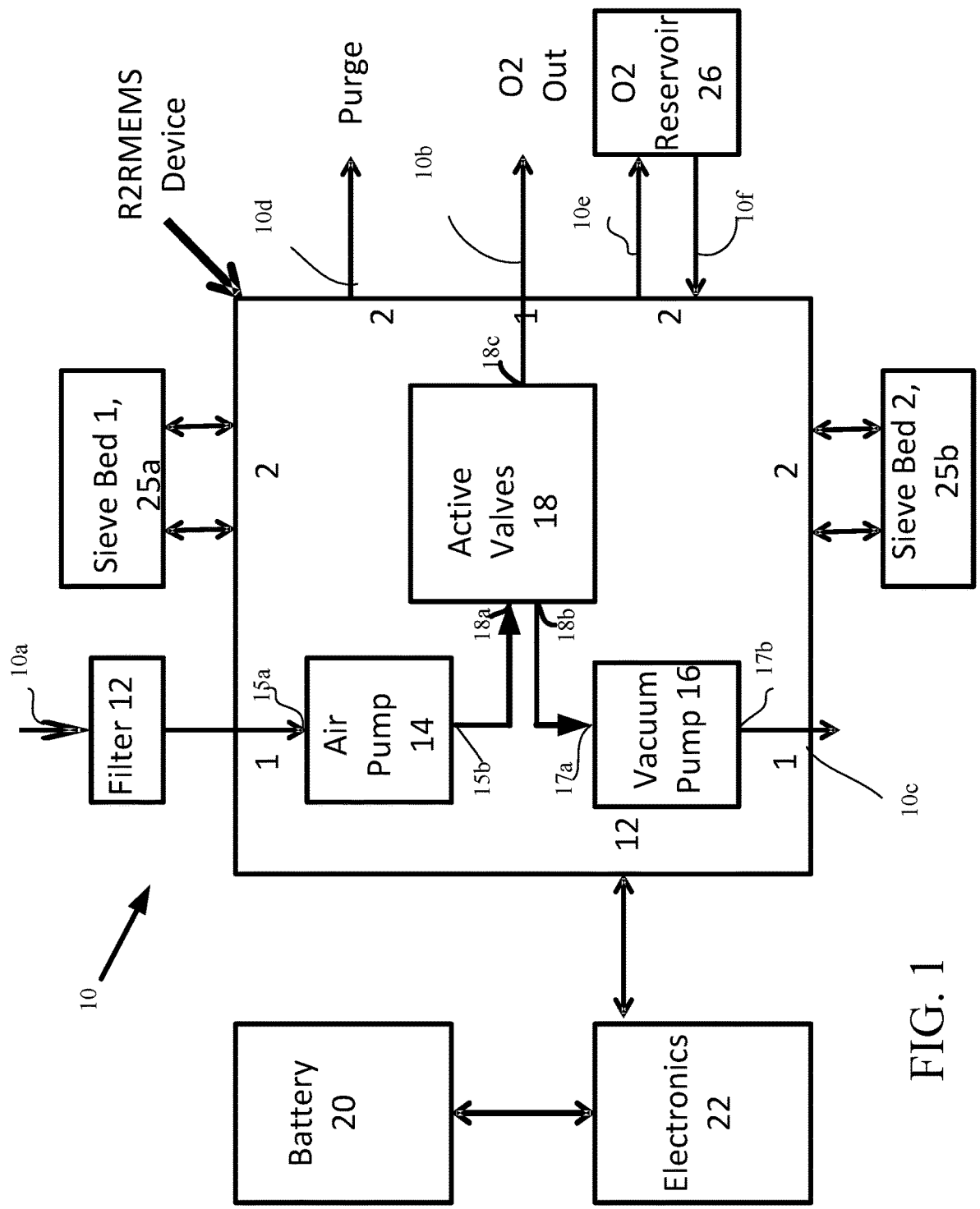
FIG. 1 is a block diagram of a microelectromechanical gas concentrator system

Referring to FIG. 1, a gas concentrator 10 is shown. The gas concentrator 10 has an input 10a, an output 10b, a vent port 10c and a purge port 10d, and in some implementations includes a pair of ports 10e, 10f coupled to an $O_2$ (oxygen) equalization reservoir 26. The gas concentrator 10 includes a filter 12, an air input multi-stage micro pump (input micro pump) 14 and a vacuum multi-stage micro pump (vacuum micro pump) 16. The gas concentrator 10 also includes active valve assembly 18, a battery 20, corresponding electronics 22, as well as sieve beds 25a, 25b, and a gas, e.g., O2 reservoir 26 (or simply an outlet of the gas concentrator). An inlet 15a of the input micro pump 14 is coupled, via filter 12, to the input 10a that is generally ambient or a gas source, an outlet 15b of the input micro pump 14 is coupled to an input 18a to the valve assembly 18. An inlet 17a of the vacuum micro pump 16 is coupled to an vent outlet 18b of the valve assembly 18 and an outlet 17b of the vacuum micro pump 16 is coupled to vent port 10c of the gas concentrator 10. In some implementations, the active valve assembly 18, air micro pump 14 and vacuum micro pump 16 are fabricated as R2R MEMS devices. In some implementations, the sieve beds 25a, 25b in addition to active valves 18, air micro pump 14 and vacuum micro pump 16 are fabricated as R2R MEMS devices. The filter 12, reservoirs 26, electronics 22 and battery 20 are typically fabricated separately. In other implementations only a single sieve bed could be used.

Figure 2A:
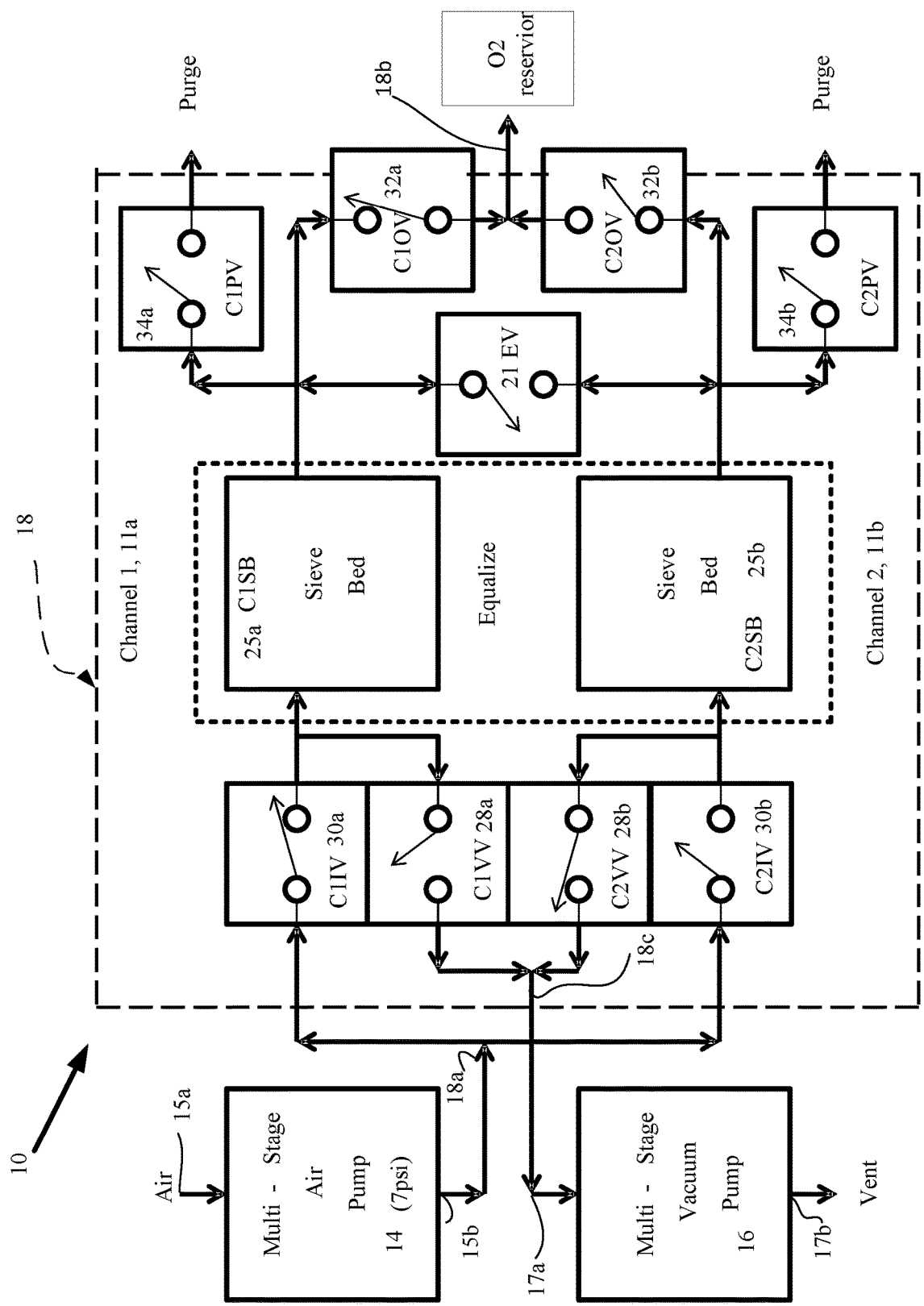
FIGS. 2A-2B are block diagrams showing an alternative that uses sensors in the microelectromechanical gas concentrator system.

Referring to FIG. 2A, the gas concentrator 10 is shown to include a first channel 11a and a second channel 11b. In FIG. 2A, each channel 11a, 11b includes corresponding connections to the input and vacuum micro pumps 14, 16. The input and vacuum micro pumps 14, 16 each include a pump body (not shown) having a single compartmentalized pump chamber (not shown) that is compartmentalized by plural membranes (not shown). In one implementation, the input and vacuum micro pumps 14, 16 are of the types described in the above mentioned incorporated by reference co-pending patent applications. The input and vacuum micro pumps 14, 16 have corresponding ports some of which are designated as inlets 15a, 17a and others of which are designated as outlets 15b, 15b. The inlet 15a of the multi-stage micro pump 14 is coupled to an ambient (or mixed gas supply) and the outlet 15b of the input micro pump 14 is coupled to the input port 18a of the valve assembly 18.

The valve assembly 18 includes valves 28a, 28b, 30a, 30b, 21, 32a, 32b, 34a and 34b. The input port 18a of the valve assembly 18 is coupled to valves C1IV 30a and C2IV 30b (corresponding to channels 1 and 2 respectively.) The inlet 17a of the vacuum micro pump 16 is coupled to the vent output 18c of the valve assembly 18, and more specifically valves 28a, 28b, and the outlet 17b of the vacuum micro pump 16 is vented. An equalizer valve 21 couples the sieve beds 25a, 25b, as shown. Channels 11a, 11b are also referred to below as "channel 1" and "channel 2."

The channel 1, 11a includes valves 28a, 30a, sieve bed 25a and valves 32a, 34a, as shown. The channel 2, 11b includes valves 28b, 30b, sieve bed 25b, and valves 32b, 34b, as shown. Each of the valves 28a, 30a, 32a, 34a and 28b, 30b, 32b, 34b has ports that act as an inlet or an outlet (not labeled), but which functions are apparent from the figures and direction arrows. Each of the sieve beds 25a, 25b and valve 21 has a pair of ports that act as input ports at certain stages of operation and output ports at other stages of operation, as will be apparent below.

Outputs from valves 28a, 28b are coupled to the input port 17a of vacuum pump 16. Valves 30a, 30b have outputs coupled to the sieve beds 25a, 25b, respectively and to the inputs of the valves 28a, 28b, as shown. The sieve beds 25a, 25b have outputs coupled to inputs of valves 32a, 34a and 34a, 34b, as shown. Valves 34a, 34b have outputs that are purge lines, whereas valves 32a, 32b have outputs that are coupled to output port(s) 18b to receive a concentrated gas. The ports could be coupled to an $O_2$ reservoir. The equalizer valve 21 is a bidirectional valve coupled between outputs of the sieve beds 25a, 25b as shown.

In some implementations, the valve assembly 18 can be constructed as a single unitary unit (comprising all valves 28a, 30a, 32a, 34a and 28b, 30b, 32b, 34b and 21) or as two unitary units, one for each channel. A first unit for the first channel would comprise valves 28a, 30a, 32a, 34a, as a first unit. A second unit for the second channel would comprise valves 28b, 30b, 32b, 34b, as a second unit. Valve 21 could be in either unit or in a separate unit.

Figure 9:
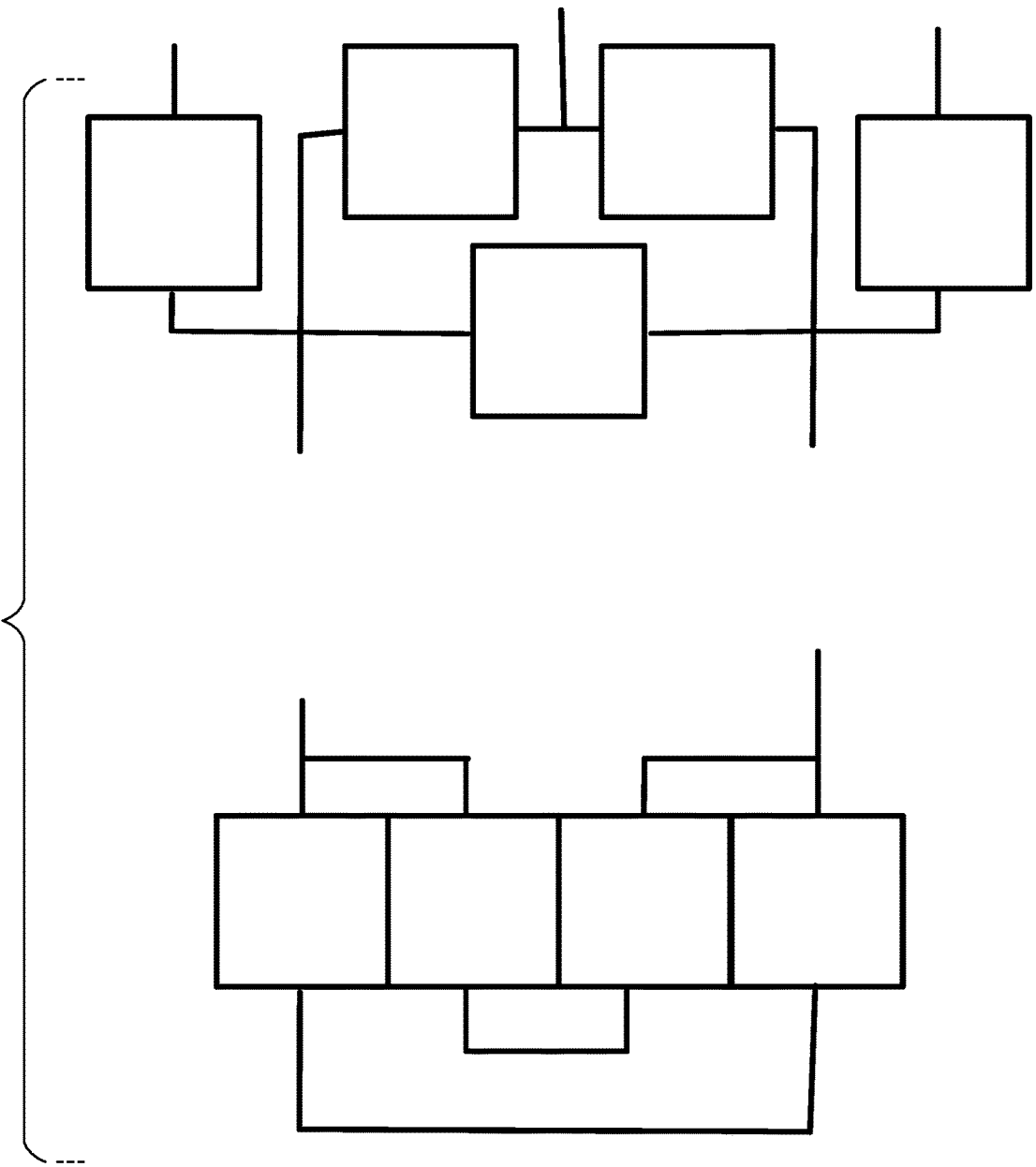
FIG. 9 is a block diagram conceptually depicting a layout or mask for a valve assembly.

In some implementations, the valve assembly 18 could also be constructed as unitary units according to other arrangements of the valves, such as in FIG. 9. The valves are micro-valves having at least two membranes that are electrostatically controlled (FIGS. 6A-6E). By a unitary unit is meant that the valves are fabricated from a common substrate or body layer and a common membrane layer and have passages through corresponding portions of the common substrate or body layer to interconnect, as appropriate, the valves in the valve assembly 18. See discussion below in FIG. 9.

Figure 2B:
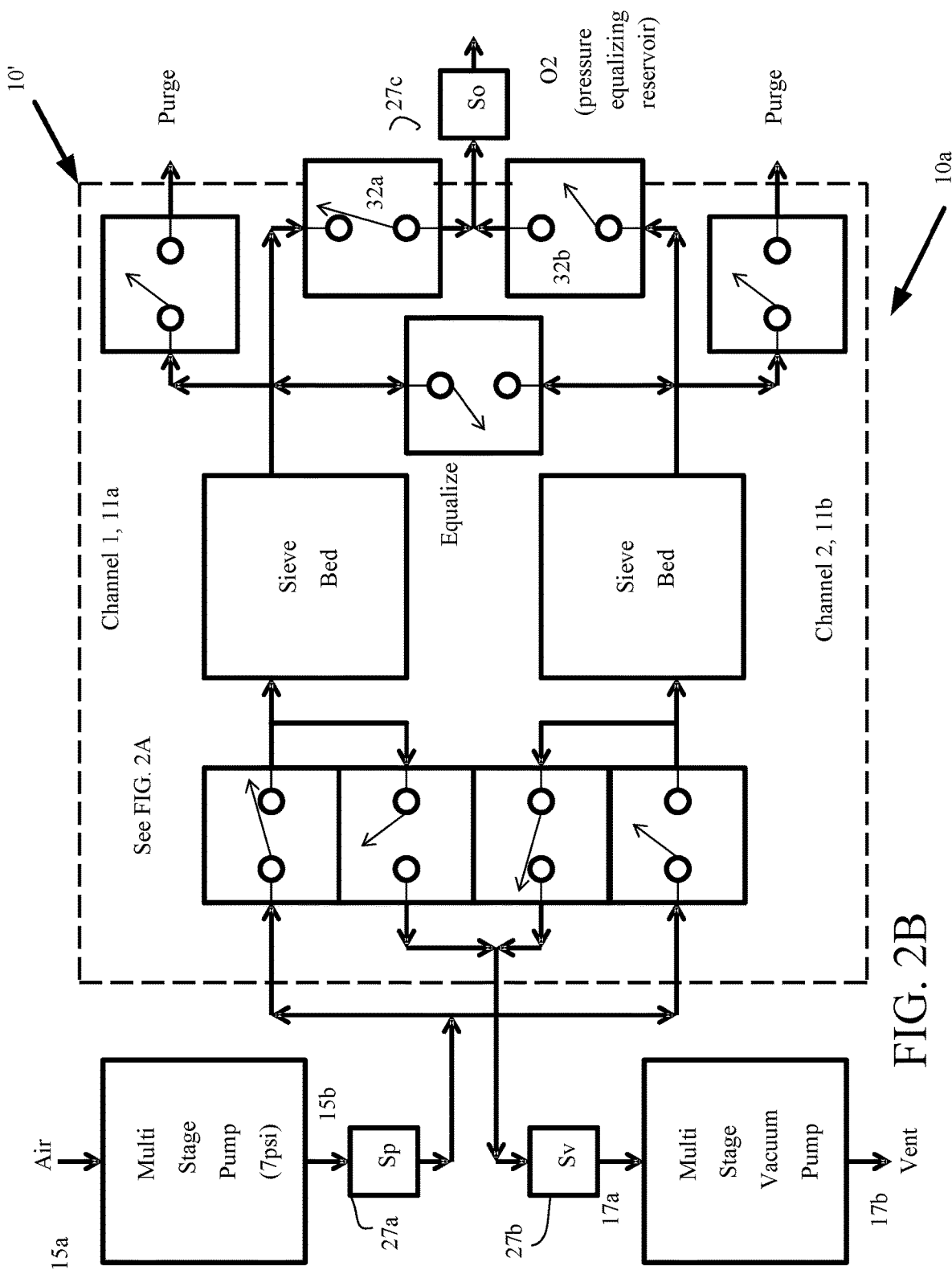

Referring to FIG. 2B, a modification 10' of the gas concentrator 10 of FIG. 2A, is shown, with a first sensor 27a interposed between the outlet 15b of the pump 14 and the inlets to the channels 11a, 11b, and a second sensor 27b interposed between an inlet 17a of the pump 16 and outlets from the first and second channels 11a, 11b. The modified gas concentrator 10a also includes a third sensor 27c coupled between the outputs of valves 32a, 32b and a reservoir (not shown) or ambient. These sensors (and or additional sensors not shown) produce sensor signals that measure pressures, flows, O2 concentrations, temperature, etc. These signals are processed by external circuitry, e.g., processor or controllers that are part of the electronics 22 (FIG. 1) to calculate from the sensor signals measures of pressures, flows, O2 concentrations, etc. that can be indicated on a display device. Together with controls these sensors can modify pressures, flows, $O_2$ concentrations, etc. These signals produce feedback for a waveform signal generator that is part of the electronics 22 that modifies timing of signals applied to the gas concentrator 10', as will be discussed below.

Figure 3:
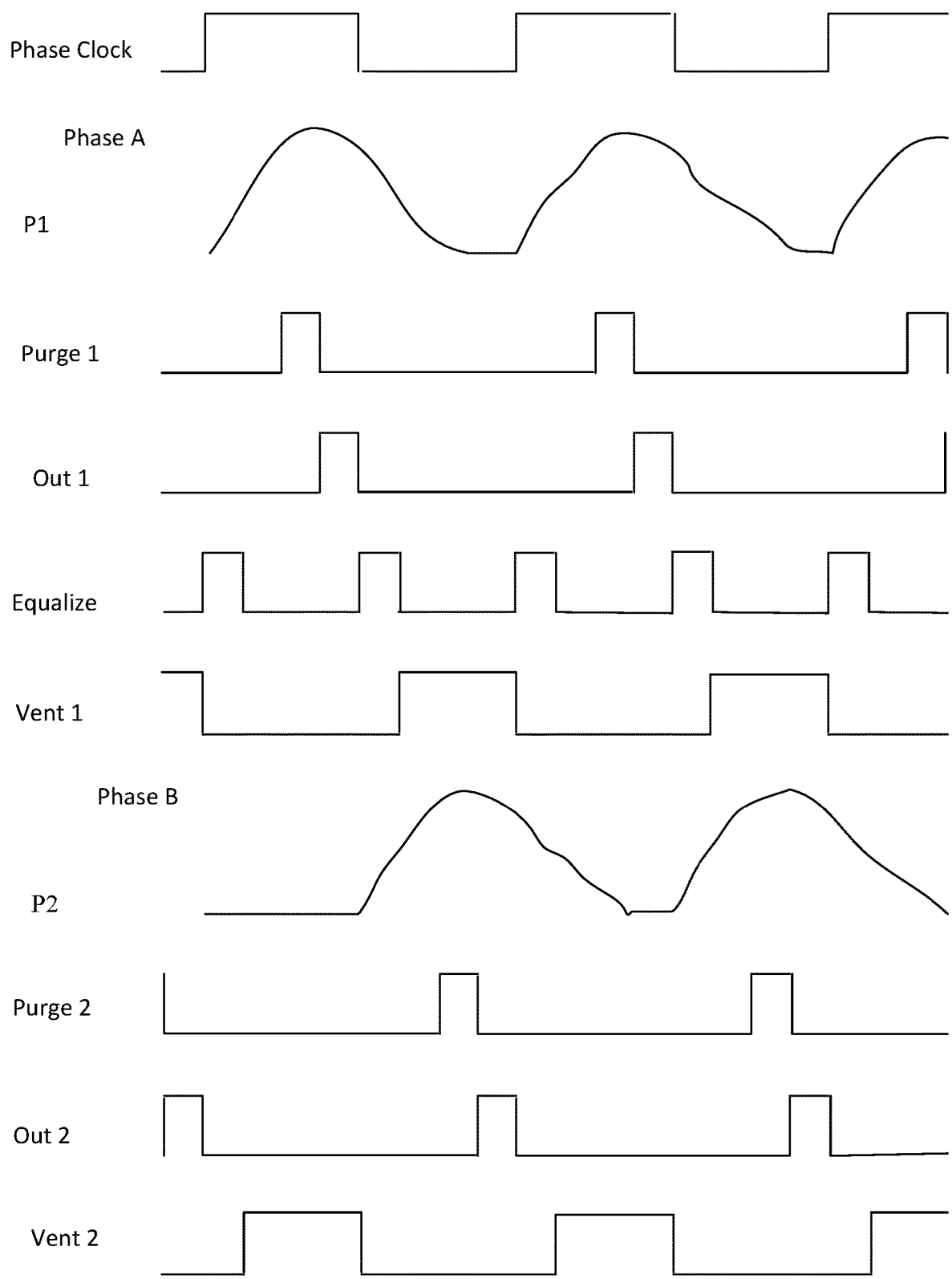
FIG. 3 is a timing diagram for the microelectromechanical gas concentrator system of FIGS. 2A-2B without purge feedback.

Referring now to FIG. 3, a timing diagram for the gas concentrator 10 (or the modified gas concentrator 10') operating according to the vacuum pressure swing adsorption (VPSA) principle, without purge air reservoir feedback is shown. The basic operation is divided into two phases A and B. A phase clock signal has two phases that are used in FIG. 3 because the gas concentrator 10 described is a two sieve bed system. If a greater number of sieve beds 25a, 25b are used, the basic timing is repeated in each phase. In some instances, the timing can be modified according to produced sensor signals by execution of algorithms, etc. that modify the timing.

Figure 3A:
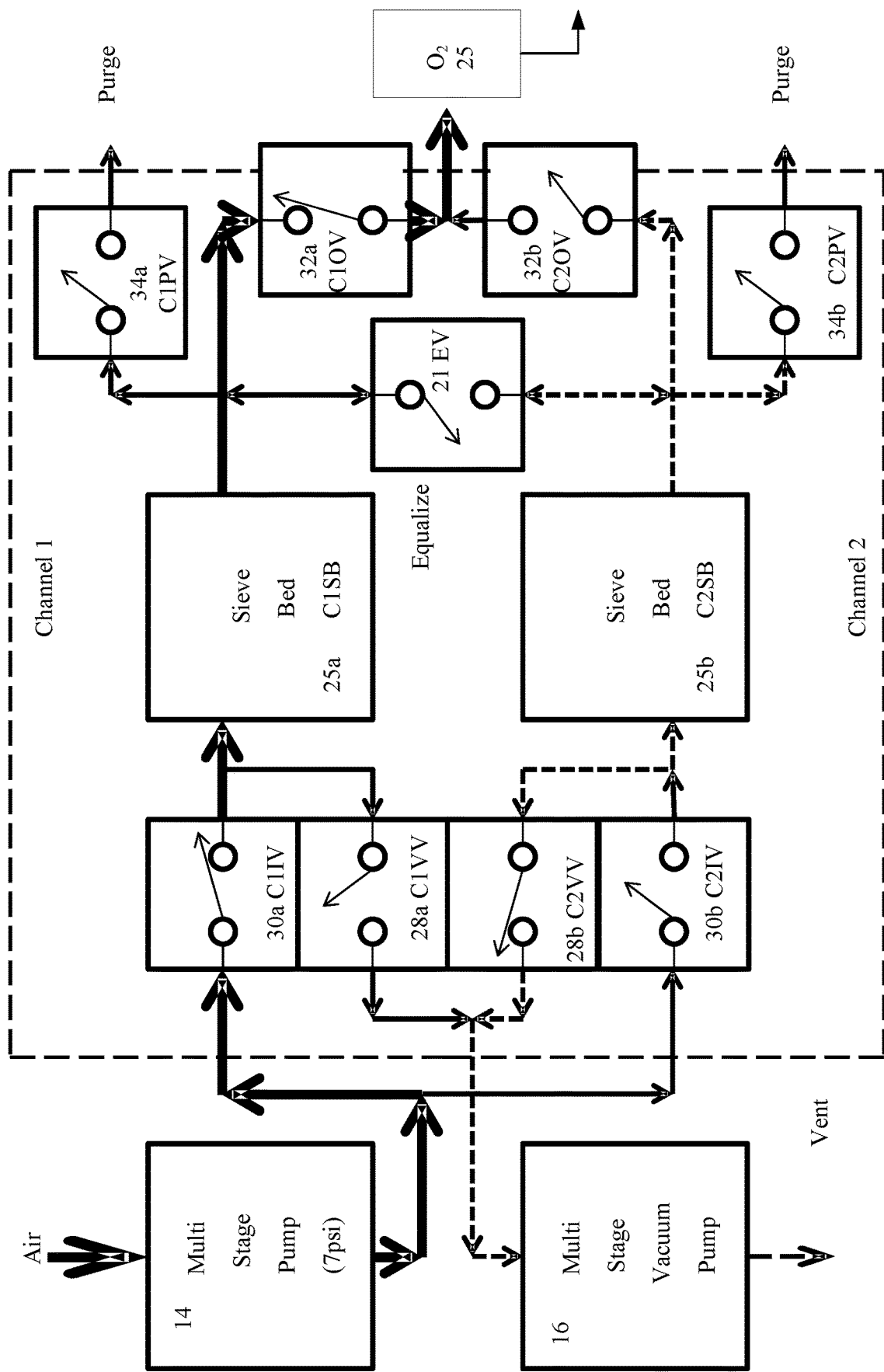
FIGS. 3A-3B are functional block diagrams of the valve arrangements for two phases of the microelectromechanical gas concentrator system.

Referring also to FIG. 3A, three paths are depicted. A first path (denoted by heavy lines) is an oxygen ($O_2$) separation path that takes air from pump 14 and delivers a concentrated stream of $O_2$ to a reservoir 25. A second path (denoted by dotted lines) is a vent path that vents nitrogen from the sieve bed 25b. A third path (denoted by narrow solid lines) is an equalization path. These paths are provided at Phase A, as follows.

The phase clock signal (Phase Clock FIG. 3), with a first phase of a cycle at an active high state) signal is applied to the input valve 30a C1IV and the complement of the phase clock signal is applied to input valve 30b C2IV. The phase clock signal closes the input valve 30a C1IV and the complement of the phase clock signal opens the input valve 30b C2IV. At substantially the same time, a true value of a vent signal (Vent 1, FIG. 3) is applied to the vent valve C2VV 28b closing the vent valve C2VV 28b, and the complement of the vent signal (Vent 1, FIG. 3) is applied the vent valve C1VV 28a opening the vent valve C1VV 28a. During active gas concentration operation of channel 1 both the air pump 14 and vacuum pump 16 are on. However, it may be possible to turn off the pumps for part of their cycle such as after either the pressure or vacuum has been achieved in order to save energy. The phase clock signal is symmetric—4 time increments (or states) high and 4 time increments (or states) low, whereas the vent signal is asymmetrical—3 time increments (or states) high and 5 time increments (or states) low.

After a period of time, e.g., less than a second up to several seconds, the pressure in the sieve bed 25a C1SB has risen to approximately the operating pressure of the pump 14 (here approximately 7 psig). During this time the purge valve 34a C1PV, output valve 32a C1OV, and equalization valve 21 EV are open. A purge signal (Purge 1, FIG. 3) is applied to have the purge valve C1PV 34a close for less than a second up to several seconds. This allows any nitrogen diluted oxygen to be purged from the output of the sieve bed 25a C1SB.

Next an output signal (Out 1, FIG. 3) is applied to the output valve 32a C1OV closing that valve for less than a second up to several seconds allowing the almost pure $O_2$ to move to the pressure equalizing reservoir 28, as shown in FIG. 3A. Once that is done, an equalization signal (Equalize, FIG. 3) is applied to the equalization valve EV 21 closing that valve for less than a second up to several seconds, to allow the partial pressurization of sieve bed 25b C2SB. The vent signal (Vent 1 FIG. 3) is applied to the vent valve 28a C1VV closing that valve such that pressure from the sieve bed 25a C1SB is vented to the ambient by the vacuum pump 12b. This sequence repeats at the beginning of the Phase Clock active high signal.

The timing of signals in the timing diagrams is relative meaning that the relationship of the signals to each other is significant, but the overall absolute cycle time can change. The overall cycle time could be defined by response times of individual components during operation. For example, assuming that a micro pump takes 0.120 seconds to pressurize a sieve bed to 7 psig, in that instance the purge or output timing could be set to 0.010 seconds, but could take substantially less time to perform.

Figure 3B:
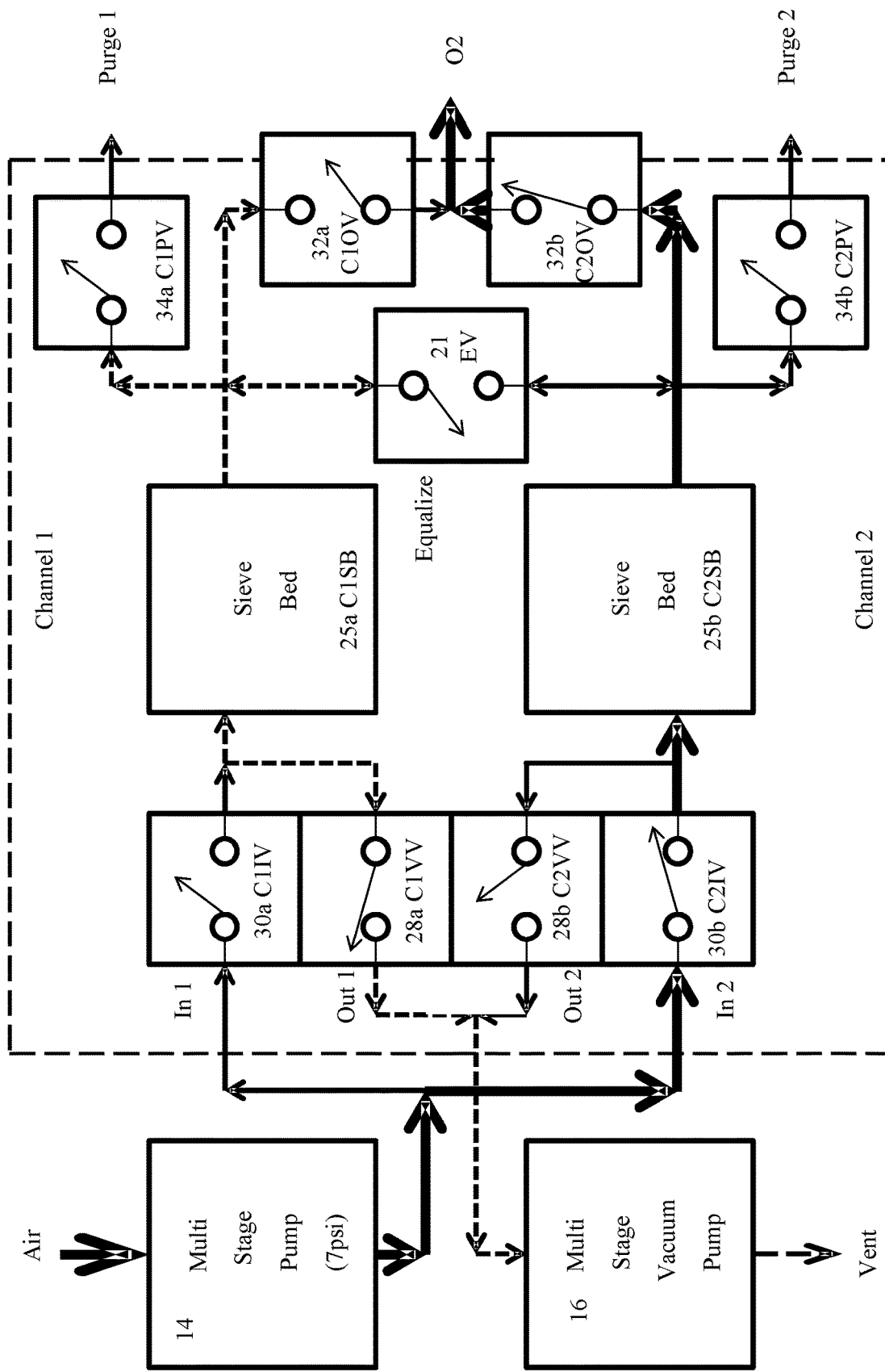

Referring to FIGS. 3, 3B looking at Phase B, it can be seen that corresponding Channel 2 valve have the same behavior as did the corresponding Channel 1 valves had during O2 separation, as discussed above, but shifted in phase. A fourth path (denoted by heavy lines) is another $O_2$ separation path that takes air from pump 14 and delivers a concentrated stream of $O_2$ to reservoir 25 in phase B. A second path (denoted by dotted lines) is a vent path that vents nitrogen from sieve bed 25a. A third path (denoted by narrow solid lines) is an equalization path. These paths are provided as follows at Phase B.

The complement of the phase clock signal (second phase of the cycle) at an active high state is applied to the input valve 30b C2IV and the input valve 30a C1IV. In this situation the complement of the phase clock signal closes the input valve 30b C2IV and opens the input valve 30a C1IV. At substantially the same time, the true value of a vent signal (Vent 2, FIG. 3) is applied to the vent valve C1VV 28a closing the vent valve C1VV 28a, and the complement of the vent signal (Vent 2, FIG. 3) is applied the vent valve C2VV 28b opening the vent valve C2VV 28b. During active gas concentration operation of channel 2, both the air pump 14 and vacuum pump 16 are on, but could be turned off for part of the cycle, as discussed above.

After less than a second up to several seconds, the pressure in the sieve bed 25b C2SB has risen to approximately the operating pressure of the pump 12a (here approximately 7 psig). During this time, the purge valve 34b C2PV, output valve 32b C2OV and equalization valve EV open. A purge signal (Purge 2, FIG. 3) is applied to have the purge valve C2PV 28b close for less than a second up to several seconds. This allows any nitrogen diluted oxygen to be purged from the output of the sieve bed 25b C2SB.

Next an output signal (Out 2, FIG. 3) is applied to the output valve 32b C2OV closing that valve for less than a second up to several seconds allowing the almost pure $O_2$ to move to the pressure equalizing reservoir 28. Once that is done, the equalization signal (Equalize, FIG. 3) is applied to the equalization valve EV 21 closing that valve for less than a second up to several seconds, to allow the partial pressurization of sieve bed 25a C1SB. The vent signal (Vent 2, FIG. 3) is applied to the vent valve 28b C2VV closing that valve such that pressure from the sieve bed 25b C2SB is vented to the ambient by the vacuum pump 12b. This sequence repeats at the beginning of the Phase Clock active low signal.

Operating metrics for such gas concentrators, e.g., an oxygen concentrator can have the air pump operate at a pressure that ranges from slightly above ambient pressure, 0 PSIG, to about 7 PSIG. Typical operating temperatures would be near ambient (more broadly between 50-90 degrees F. or other ranges) with a slight amount self-heating. A typical cycle time would be in a range of less than a second to about 7 seconds. The minimum on the cycle time range would be governed by response times of individual functions, whereas the maximum on the cycle time range would be governed by the application of the gas concentrator 10 and material properties of the individual components. For breathing applications the cycle time would be fast enough to keep up with a person's breathing rate. The adsorption rate would be driven by the operating pressure of the pump 14 and the desorption rate would be driven by the extent of vacuum produced by the pump 16.

The adsorption capacity (expressed in ml/g is a characteristic of the adsorption material). The amount of material and sieve geometry would be selected to produce a desired production rate of ml/s (second) characteristic. Flow rates would be around 4-5 liters per minute—sufficient to keep up with breathing and the mode of operation would be either continuous or pulsed to conserve energy in battery operations. The $O_2$ concentration percentage could be above 90% or more if required. The weight of the gas concentrators most likely is driven by battery weight as the remaining components are relatively light. The overall weight would be relatively light in comparison with current commercially available oxygen concentrators. The overall size would be comparatively small in comparison with current commercially available oxygen concentrators and most likely driven by sieve bed and/or battery size. The cost would be relatively inexpensive in comparison with commercially available oxygen concentrators.

Figure 4:
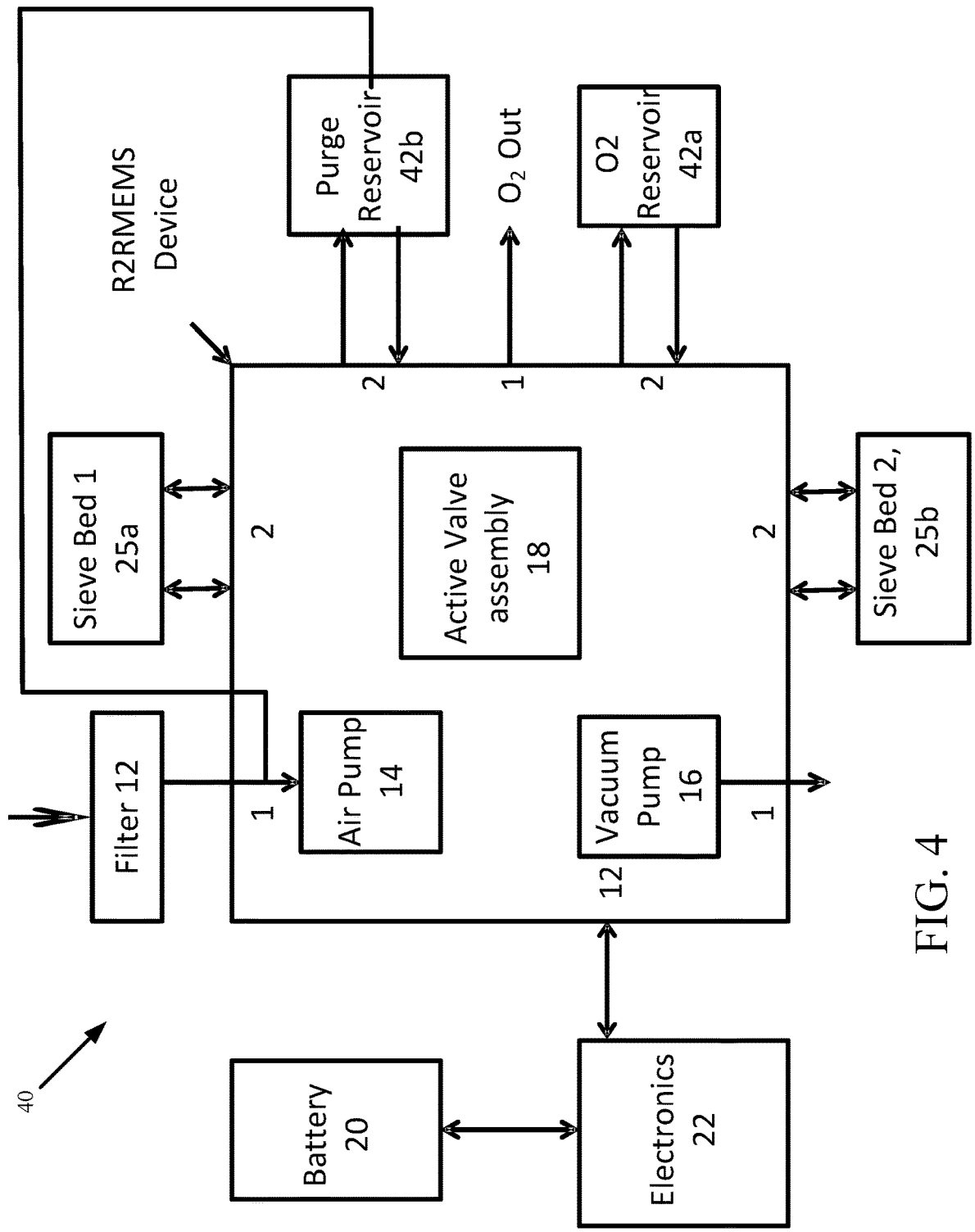
FIG. 4 is a block diagram of a microelectromechanical gas concentrator system with purge gas feedback.

Referring now to FIG. 4, an alternative gas concentrator 40 is shown. The gas concentrator 40 includes the filter 12, an air micro pump 14 and a vacuum micro pump 16. The gas concentrator 40 also includes active valves (assembly 18), a battery 20, corresponding electronics 22, as well as sieve beds 25a, 25b, and a gas, e.g., $O_2$ reservoir 42a, generally as in FIG. 1. In addition, gas concentrator 40 also includes a purge reservoir 42b and purge feedback. The purge reservoir 42b receives gas from the active valves 18 and feeds that gas back to the air pump. The inlet 17a of the vacuum micro pump 16 is coupled to valves 28a, 28b and the outlet 17b of the vacuum micro pump 16 is vented. In some implementations, the valves, sensors, and pumps are fabricated as R2R MEMS devices. In some implementations, the sieve beds 25a, 25b in addition to the valves and pumps are fabricated as R2R MEMS devices. The filter 12, reservoirs 42a, 42b, the electronics 22 and battery 20 are fabricated separately. While not shown, sensors, as in modified gas concentrator 10', can also be used with the alternative gas concentrator 40.

FIGS. 4A-4D show the operation during phase A of the valves in valve assembly 18 in more detail, while FIGS. 4E-4H show the operation during phase B of the valves in more detail. In FIGS. 4A-4H the purge reservoir 42b can be inferred (implementing Function 1 and Function 2 in the tables below or can be excluded (implementing only Function 1 in the tables below). Also in FIG. 4A-4D and FIGS. 4E-4H the valves are pictorially shown as either open or closed according to the phase A, B and sub-phase A1-A4 and B1-B4 and operation of those valves is summarized in the tables below:

| Operation State A1 (FIG. 4A) | | | |
|---|---|---|---|
| Operation: | Element | Status: | Description: |
| Phase: | A | | |
| State: | A1 | | |
| Air Pump | AP | on | Compressing air to operating pressure into a sieve bed for separation |
| Vacuum Pump | VP | on | Evacuating air to negative operating pressure from a sieve bed for regeneration |
| Purge Reservoir | PR | inactive | Used to set the pressure in a sieve bed to ambient - saves energy |
| O2 Reservoir | OR | inactive | Used to hold produced O2 and to lower the pressure to near ambient |
| Equalization Valve | EV | open | Used to pre-pressurize the next sieve bed separation phase - saves energy |
| Channel: | 1 | | |
| Sieve Bed | C1SB | pressurizing | Sized for ½ of total required O2 production |
| Input Valve | C1IV | open | Passes compressed air into sieve bed |
| Purge Valve | C1PV | closed | Function 1: releases diluted O2 before O2 harvest: to Purge Reservoir |
| | | | Function 2: returns next sieve bed separation phase to ambient: from Purge Reservoir |
| Output Valve | C1OV | closed | Passes generated O2 to O2 Reservoir |
| Vent Valve | C1VV | closed | Passes pressure from sieve bed to vacuum pump |
| Channel: | 2 | | |
| Sieve Bed | C2SB | de-pressurizing | Sized for ½ of total required O2 production |
| Input Valve | C2IV | closed | Passes compressed air into sieve bed |

-continued

Figure 4A:
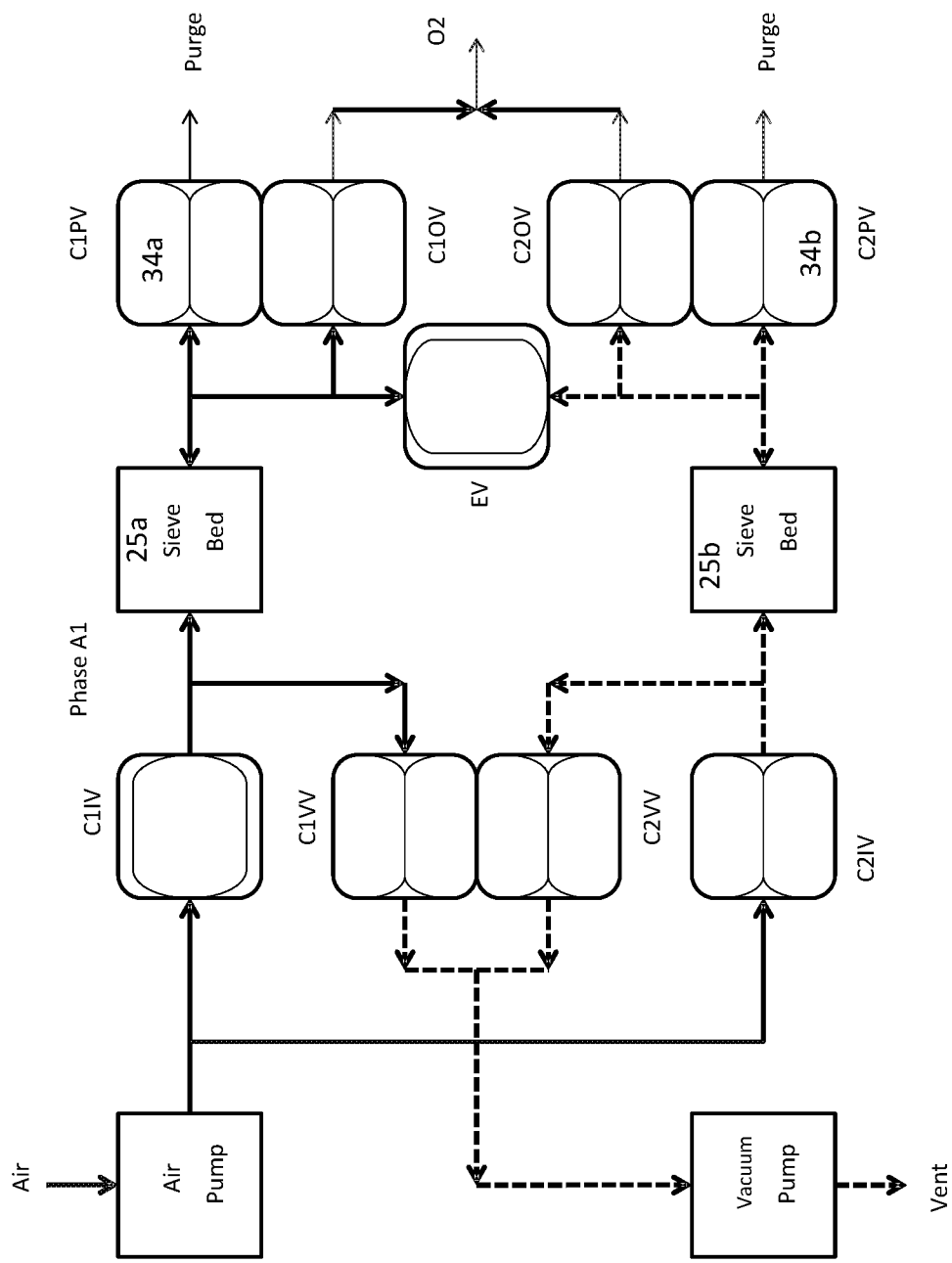
FIGS. 4A-4H are functional block diagrams of the valve arrangements for the two phases of the microelectromechanical gas concentrator system

Operation State A1 (FIG. 4A)

| Operation: | Element | Status: | Description: |
|---|---|---|---|
| Purge Valve | C2PV | closed | Function 1: releases diluted O2 before O2 harvest: to Purge Reservoir |
| | | | Function 2: returns next sieve bed separation phase to ambient: from Purge Reservoir |
| Output Valve | C2OV | closed | Passes generated O2 to O2 Reservoir |
| Vent Valve | C2VV | closed | Passes pressure from sieve bed to vacuum pump |

Figure 4B:
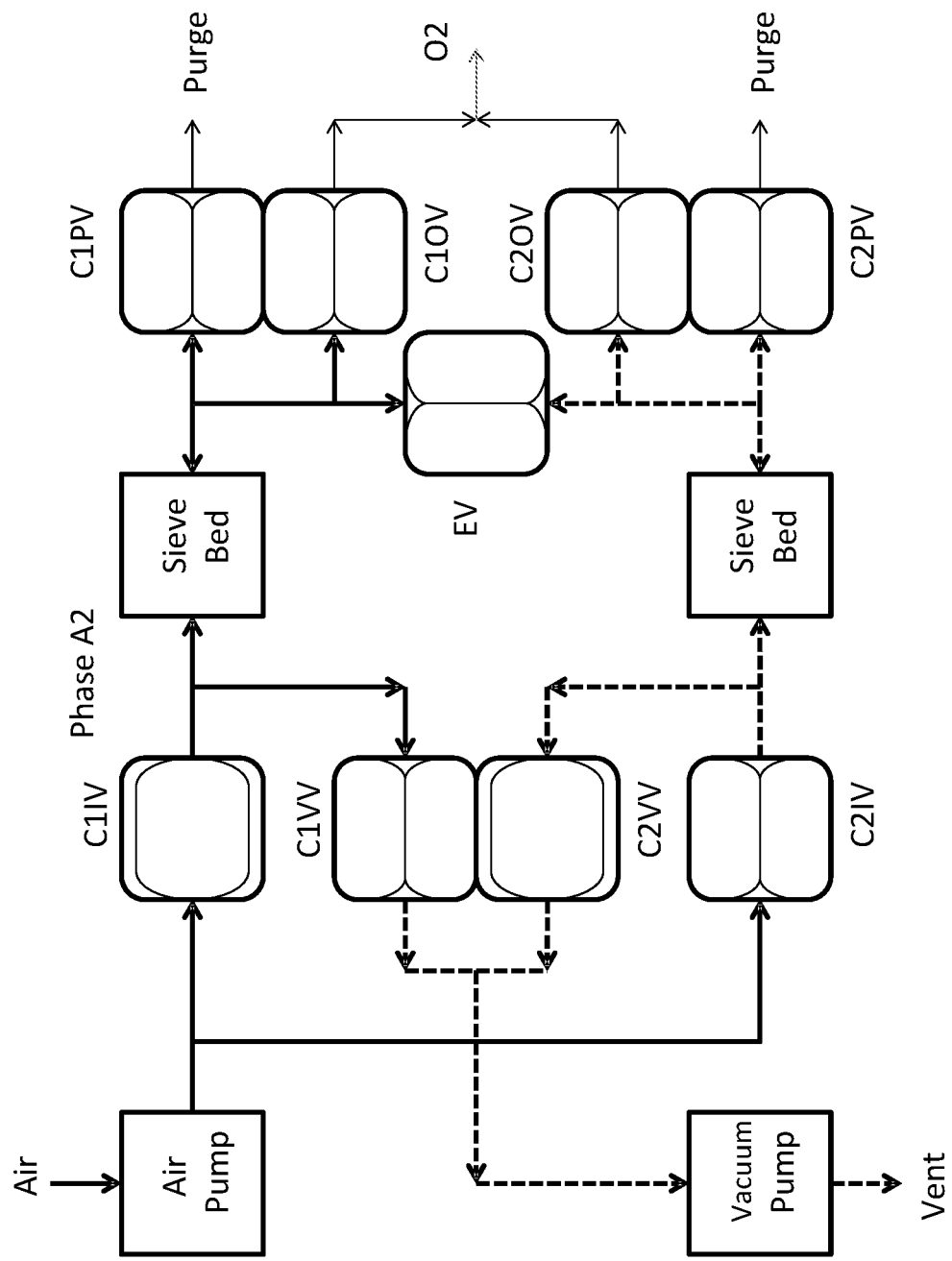

Operation State A2 (FIG. 4B)

| Operation: | Separation | Status: | Description: |
|---|---|---|---|
| Phase: | A | | |
| State: | A2 | | |
| Air Pump | AP | on | Compressing air to operating pressure into a sieve bed for separation |
| Vacuum Pump | VP | on | Evacuating air to negative operating pressure from a sieve bed for regeneration |
| Purge Reservoir | PR | inactive | Used to set the pressure in a sieve bed to ambient - saves energy |
| O2 Reservoir | OR | inactive | Used to hold produced O2 and to lower the pressure to near ambient |
| Equalization Valve | EV | closed | Used to pre-pressurize the next sieve bed separation phase - saves energy |
| Channel: | 1 | | |
| Sieve Bed | C1SB | pressurizing | Sized for ½ of total required O2 production |
| Input Valve | C1IV | open | Passes compressed air into sieve bed |
| Purge Valve | C1PV | closed | Function1: releases diluted O2 before O2 harvest: to Purge Reservoir |
| | | | Function2: returns next sieve bed separation phase to ambient: from Purge Reservoir |
| Output Valve | C1OV | closed | Passes generated O2 to O2 Reservoir |
| Vent Valve | C1VV | closed | Passes pressure from sieve bed to vacuum pump |
| Channel: | 2 | | |
| Sieve Bed | C2SB | de-pressurizing | Sized for ½ of total required O2 production |
| Input Valve | C2IV | closed | Passes compressed air into sieve bed |
| Purge Valve | C2PV | closed | Function 1: releases diluted O2 before O2 harvest: to Purge Reservoir |
| | | | Function 2: returns next sieve bed separation phase to ambient: from Purge Reservoir |
| Output Valve | C2OV | closed | Passes generated O2 to O2 Reservoir |
| Vent Valve | C2VV | open | Passes pressure from sieve bed to vacuum pump |

Figure 4C:
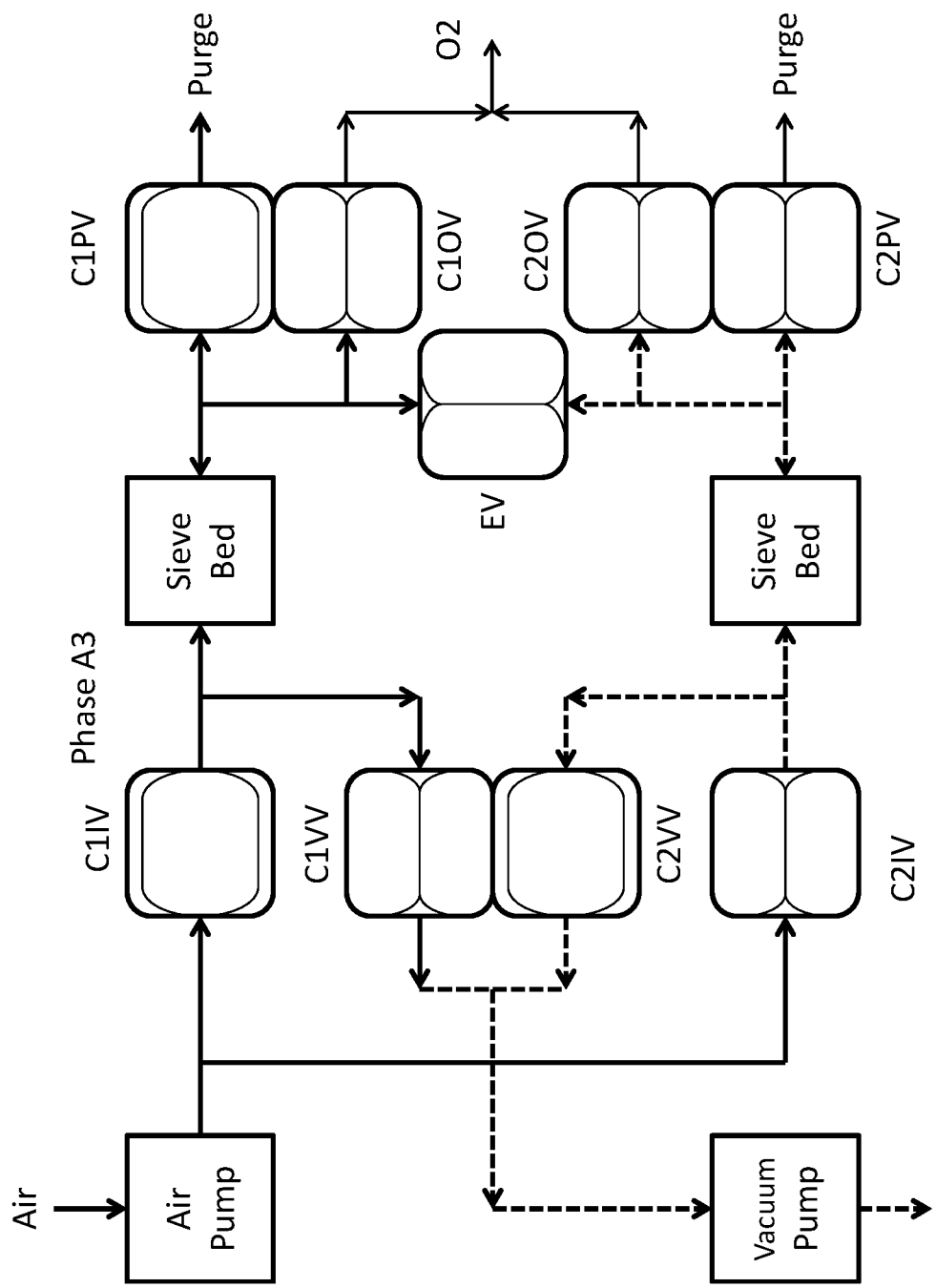

Operation State A3 (FIG. 4C)

| Operation: | Separation | Status: | Description: |
|---|---|---|---|
| Phase: | A | | |
| State: | A3 | | |
| Air Pump | AP | on | Compressing air to operating pressure into a sieve bed for separation |
| Vacuum Pump | VP | on | Evacuating air to negative operating pressure from a sieve bed for regeneration |
| Purge Reservoir | PR | inactive | Used to set the pressure in a sieve bed to ambient - saves energy |
| O2 Reservoir | OR | inactive | Used to hold produced O2 and to lower the pressure to near ambient |
| Equalization Valve | EV | closed | Used to pre-pressurize the next sieve bed separation phase - saves energy |
| Channel: | 1 | | |
| Sieve Bed | C1SB | pressurizing> | Sized for ½ of total required O2 production |
| Input Valve | C1IV | open | Passes compressed air into sieve bed |
| Purge Valve | C1PV | open-function1 | Function 1: releases diluted O2 before O2 harvest: to Purge Reservoir |
| | | | Function 2: returns next sieve bed separation phase to ambient: from Purge Reservoir |
| Output Valve | C1OV | closed | Passes generated O2 to O2 Reservoir |
| Vent Valve | C1VV | closed | Passes pressure from sieve bed to vacuum pump |
| Channel: | 2 | | |
| Sieve Bed | C2SB | de-pressurizing | Sized for ½ of total required O2 production |
| Input Valve | C2IV | closed | Passes compressed air into sieve bed |
| Purge Valve | C2PV | closed | Function 1: releases diluted O2 before O2 harvest: to Purge Reservoir |
| | | | Function 2: returns next sieve bed separation phase to ambient: from Purge Reservoir |
| Output Valve | C2OV | closed | Passes generated O2 to O2 Reservoir |
| Vent Valve | C2VV | open | Passes pressure from sieve bed to vacuum pump |

Figure 4D:
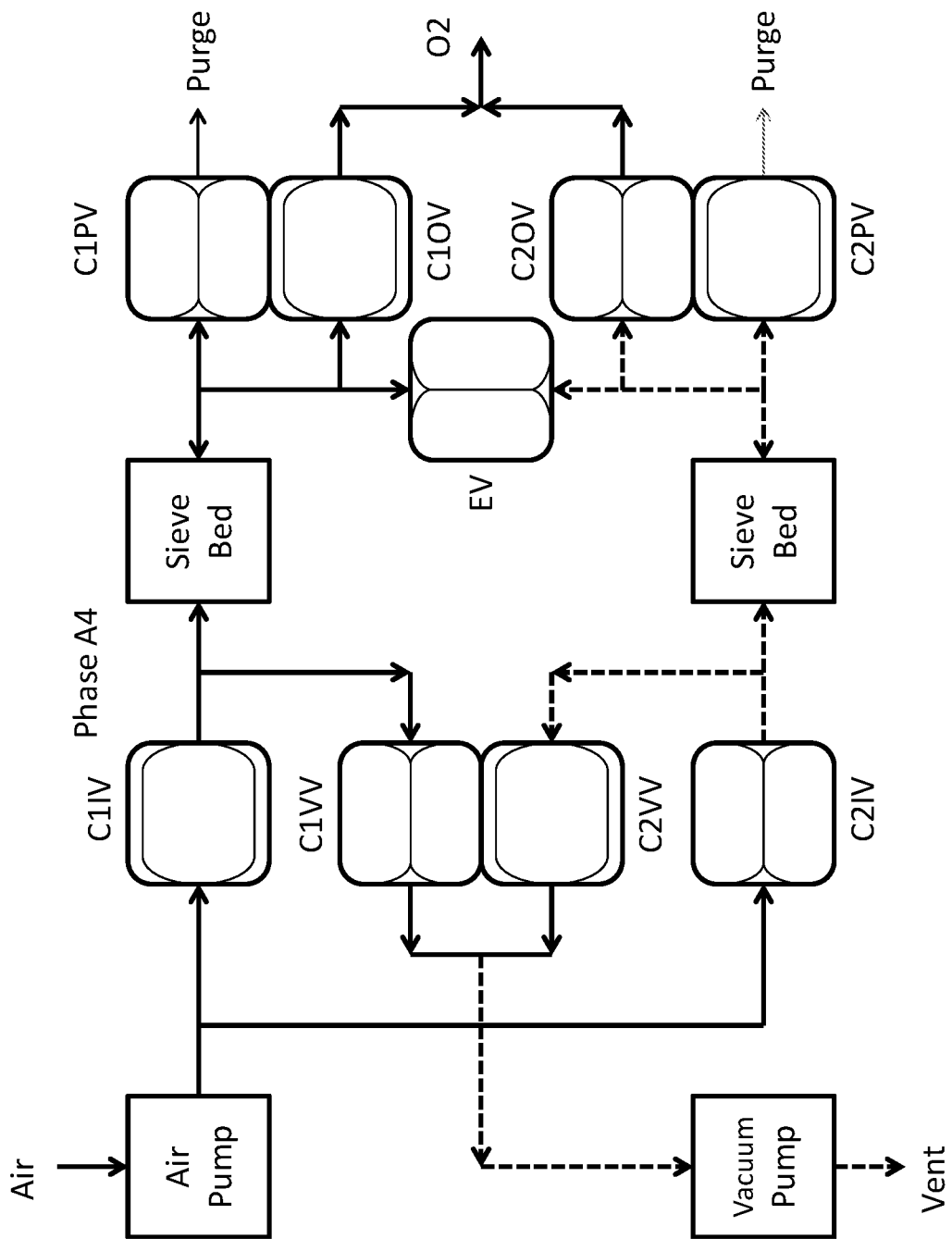

Operation State A4 (FIG. 4D)

| Operation: | Separation | Status: | Description: |
|---|---|---|---|
| Phase: | A | | |
| State: | A4 | | |
| Air Pump | AP | on | Compressing air to operating pressure into a sieve bed for separation |
| Vacuum Pump | VP | on | Evacuating air to negative operating pressure from a sieve bed for regeneration |
| Purge Reservoir | PR | inactive | Used to set the pressure in a sieve bed to ambient - saves energy |
| O2 Reservoir | OR | inactive | Used to hold produced O2 and to lower the pressure to near ambient |
| Equalization Valve | EV | closed | Used to pre-pressurize the next sieve bed separation phase - saves energy |
| Channel: | 1 | | |
| Sieve Bed | C1SB | pressurizing> | Sized for ½ of total required O2 production |
| Input Valve | C1IV | open | Passes compressed air into sieve bed |
| Purge Valve | C1PV | closed | Function 1: releases diluted O2 before O2 harvest: to Purge Reservoir |
| | | | Function 2: returns next sieve bed separation phase to ambient: from Purge Reservoir |
| Output Valve | C1OV | open | Passes generated O2 to O2 Reservoir |
| Vent Valve | C1VV | closed | Passes pressure from sieve bed to vacuum pump |
| Channel: | 2 | | |
| Sieve Bed | C2SB | de-pressurizing | Sized for ½ of total required O2 production |
| Input Valve | C2IV | closed | Passes compressed air into sieve bed |
| Purge Valve | C2PV | open-function2 | Function 1: releases diluted O2 before O2 harvest: to Purge Reservoir |
| | | | Function 2: returns next sieve bed separation phase to ambient: from Purge Reservoir |
| Output Valve | C2OV | closed | Passes generated O2 to O2 Reservoir |
| Vent Valve | C2VV | open | Passes pressure from sieve bed to vacuum pump |

Figure 4E:
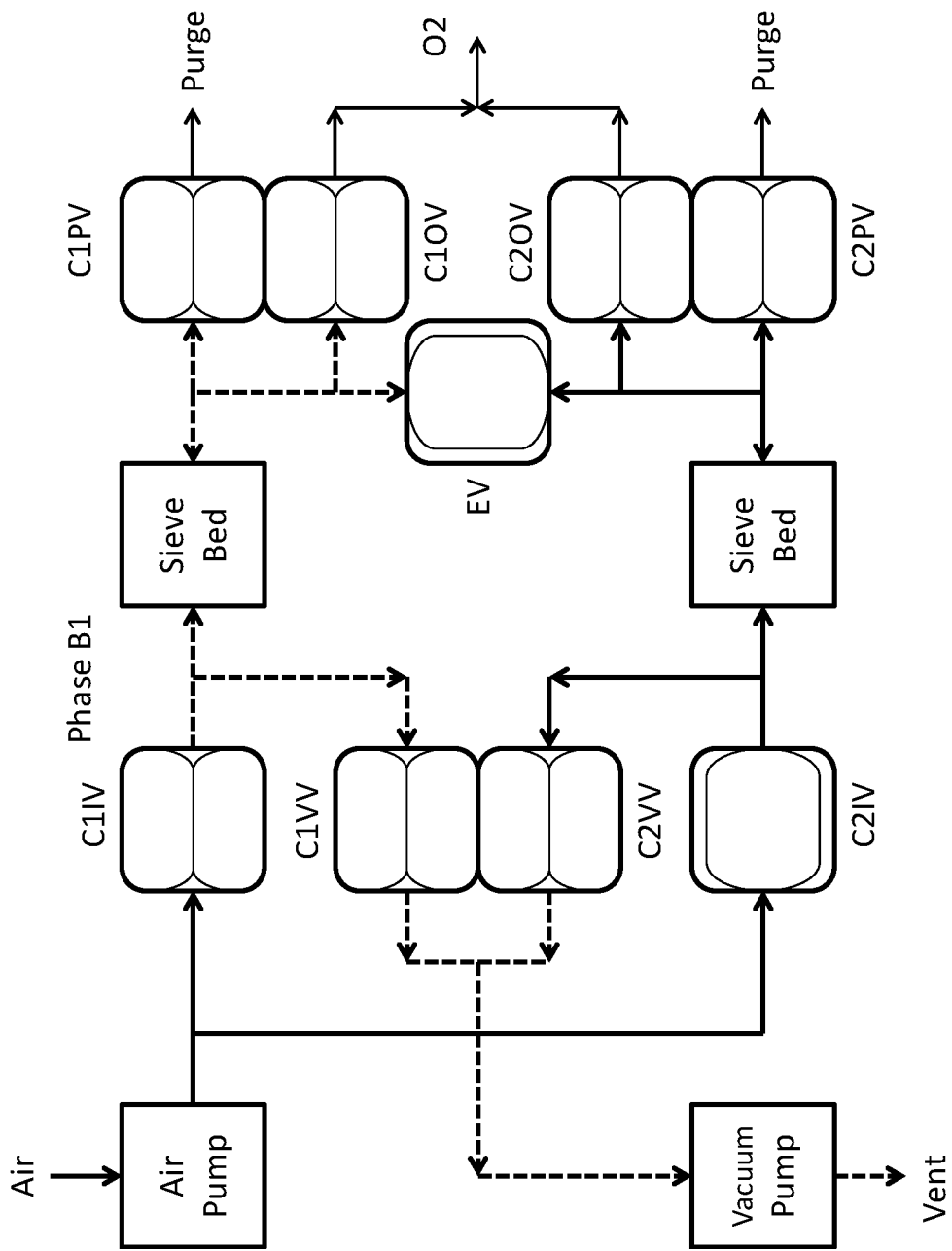

Similarly for Channel 2 phase B is as follows:

Operation State B1 (FIG. 4E)

| Operation: | Separation | Status: | Description: |
|---|---|---|---|
| Phase: | B | | |
| State: | B1 | | |
| Air Pump | AP | on | Compressing air to operating pressure into a sieve bed for separation |
| Vacuum Pump | VP | on | Evacuating air to negative operating pressure from a sieve bed for regeneration |
| Purge Reservoir | PR | inactive | Used to set the pressure in a sieve bed to ambient - saves energy |
| O2 Reservoir | OR | inactive | Used to hold produced O2 and to lower the pressure to near ambient |
| Equalization Valve | EV | open | Used to pre-pressurize the next sieve bed separation phase - saves energy |
| Channel: | 1 | | |
| Sieve Bed | C1SB | de-pressurizing | Sized for ½ of total required O2 production |
| Input Valve | C1IV | closed | Passes compressed air into sieve bed |
| Purge Valve | C1PV | closed | Function 1: releases diluted O2 before O2 harvest: to Purge Reservoir |
| | | | Function 2: returns next sieve bed separation phase to ambient: from Purge Reservoir |
| Output Valve | C1OV | closed | Passes generated O2 to O2 Reservoir |
| Vent Valve | C1VV | closed | Passes pressure from sieve bed to vacuum pump |
| Channel: | 2 | | |
| Sieve Bed | C2SB | pressurizing | Sized for ½ of total required O2 production |
| Input Valve | C2IV | open | Passes compressed air into sieve bed |
| Purge Valve | C2PV | closed | Function 1: releases diluted O2 before O2 harvest: to Purge Reservoir |
| | | | Function 2: returns next sieve bed separation phase to ambient: from Purge Reservoir |
| Output Valve | C2OV | closed | Passes generated O2 to O2 Reservoir |
| Vent Valve | C2VV | closed | Passes pressure from sieve bed to vacuum pump |

Figure 4F:
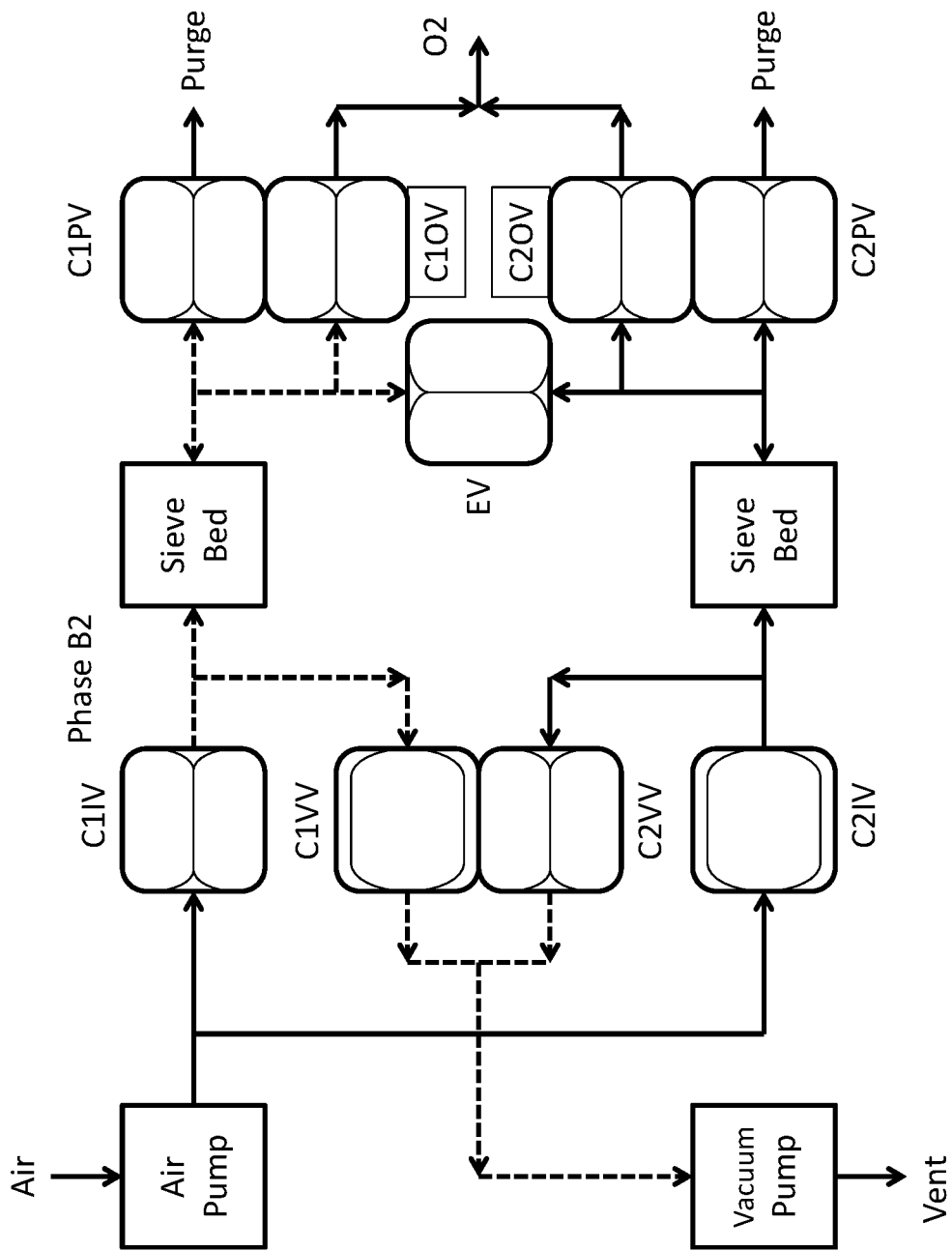

Operation State B2 (FIG. 4F)

| Operation: | Separation | Status: | Description: |
|---|---|---|---|
| Phase: | B | | |
| State: | B2 | | |
| Air Pump | AP | on | Compressing air to operating pressure into a sieve bed for separation |
| Vacuum Pump | VP | on | Evacuating air to negative operating pressure from a sieve bed for regeneration |
| Purge Reservoir | PR | inactive | Used to set the pressure in a sieve bed to ambient - saves energy |
| O2 Reservoir | OR | inactive | Used to hold produced O2 and to lower the pressure to near ambient |
| Equalization Valve | EV | closed | Used to pre-pressurize the next sieve bed separation phase - saves energy |
| Channel: | 1 | | |
| Sieve Bed | C1SB | de-pressurizing | Sized for ½ of total required O2 production |
| Input Valve | C1IV | closed | Passes compressed air into sieve bed |
| Purge Valve | C1PV | closed | Function 1: releases diluted O2 before O2 harvest: to Purge Reservoir |
| | | | Function 2: returns next sieve bed separation phase to ambient: from Purge Reservoir |

Operation State B2 (FIG. 4F)

| Operation: | Separation | Status: | Description: |
|---|---|---|---|
| Output Valve | C1OV | closed | Passes generated O2 to O2 Reservoir |
| Vent Valve | C1VV | open | Passes pressure from sieve bed to vacuum pump |
| Channel: | 2 | | |
| Sieve Bed | C2SB | pressurizing | Sized for ½ of total required O2 production |
| Input Valve | C2IV | open | Passes compressed air into sieve bed |
| Purge Valve | C2PV | closed | Function 1: releases diluted O2 before O2 harvest: to Purge Reservoir |
| | | | Function 2: returns next sieve bed separation phase to ambient: from Purge Reservoir |
| Output Valve | C2OV | closed | Passes generated O2 to O2 Reservoir |
| Vent Valve | C2VV | closed | Passes pressure from sieve bed to vacuum pump |

Figure 4G:
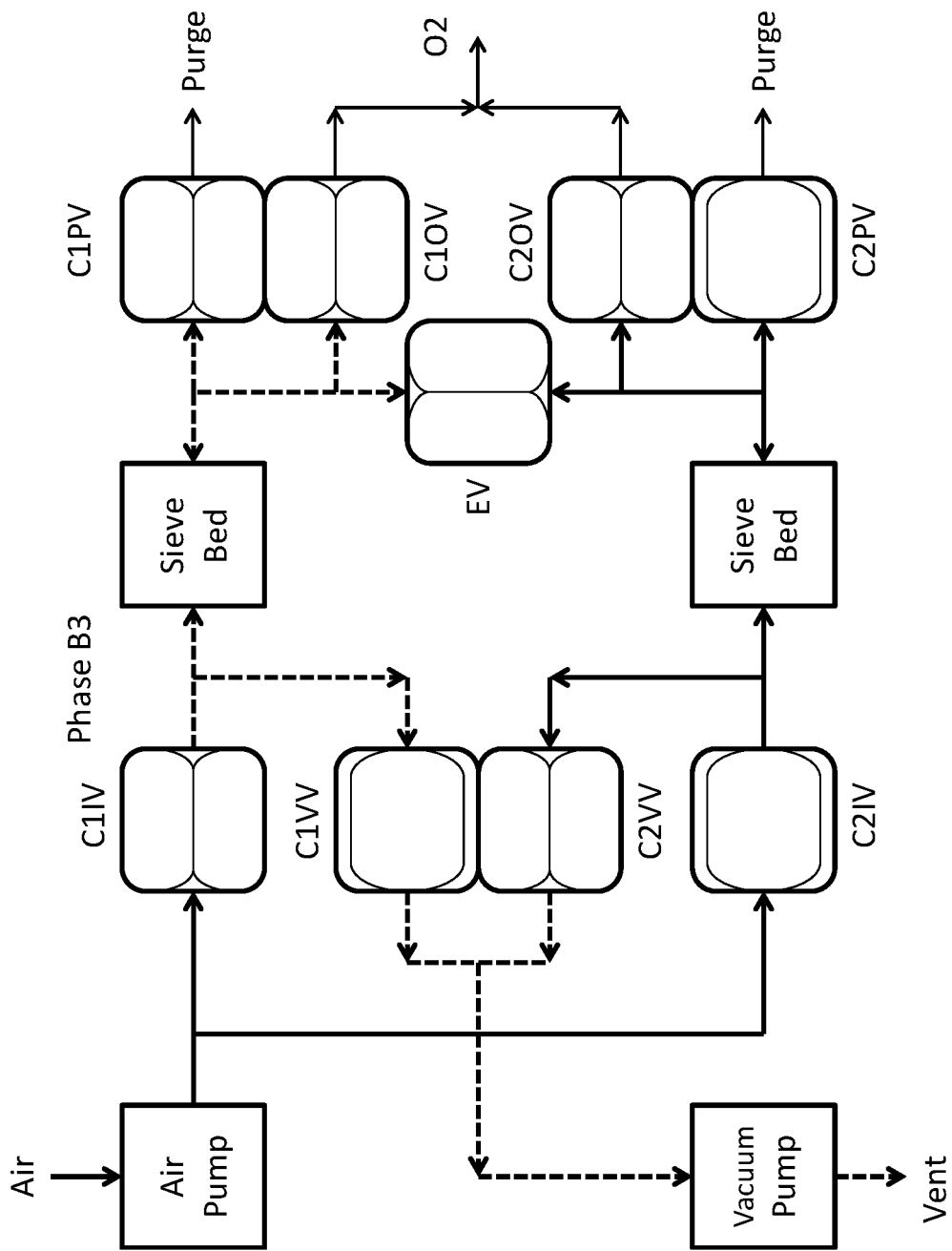

Operation State B3 (FIG. 4G)

| Operation: | Separation | Status: | Description: |
|---|---|---|---|
| Phase: | B | | |
| State: | B3 | | |
| Air Pump | AP | on | Compressing air to operating pressure into a sieve bed for separation |
| Vacuum Pump | VP | on | Evacuating air to negative operating pressure from a sieve bed for regeneration |
| Purge Reservoir | PR | inactive | Used to set the pressure in a sieve bed to ambient - saves energy |
| O2 Reservoir | OR | inactive | Used to hold produced O2 and to lower the pressure to near ambient |
| Equalization Valve | EV | closed | Used to pre-pressurize the next sieve bed separation phase - saves energy |
| Channel: | 1 | | |
| Sieve Bed | C1SB | de-pressurizing | Sized for ½ of total required O2 production |
| Input Valve | C1IV | closed | Passes compressed air into sieve bed |
| Purge Valve | C1PV | closed | Function 1: releases diluted O2 before O2 harvest: to Purge Reservoir |
| | | | Function 2: returns next sieve bed separation phase to ambient: from Purge Reservoir |
| Output Valve | C1OV | closed | Passes generated O2 to O2 Reservoir |
| Vent Valve | C1VV | open | Passes pressure from sieve bed to vacuum pump |
| Channel: | 2 | | |
| Sieve Bed | C2SB | pressurizing> | Sized for ½ of total required O2 production |
| Input Valve | C2IV | open | Passes compressed air into sieve bed |
| Purge Valve | C2PV | open-function1 | Function 1: releases diluted O2 before O2 harvest: to Purge Reservoir |
| | | | Function 2: returns next sieve bed separation phase to ambient: from Purge Reservoir |
| Output Valve | C2OV | closed | Passes generated O2 to O2 Reservoir |
| Vent Valve | C2VV | closed | Passes pressure from sieve bed to vacuum pump |

Figure 4H:
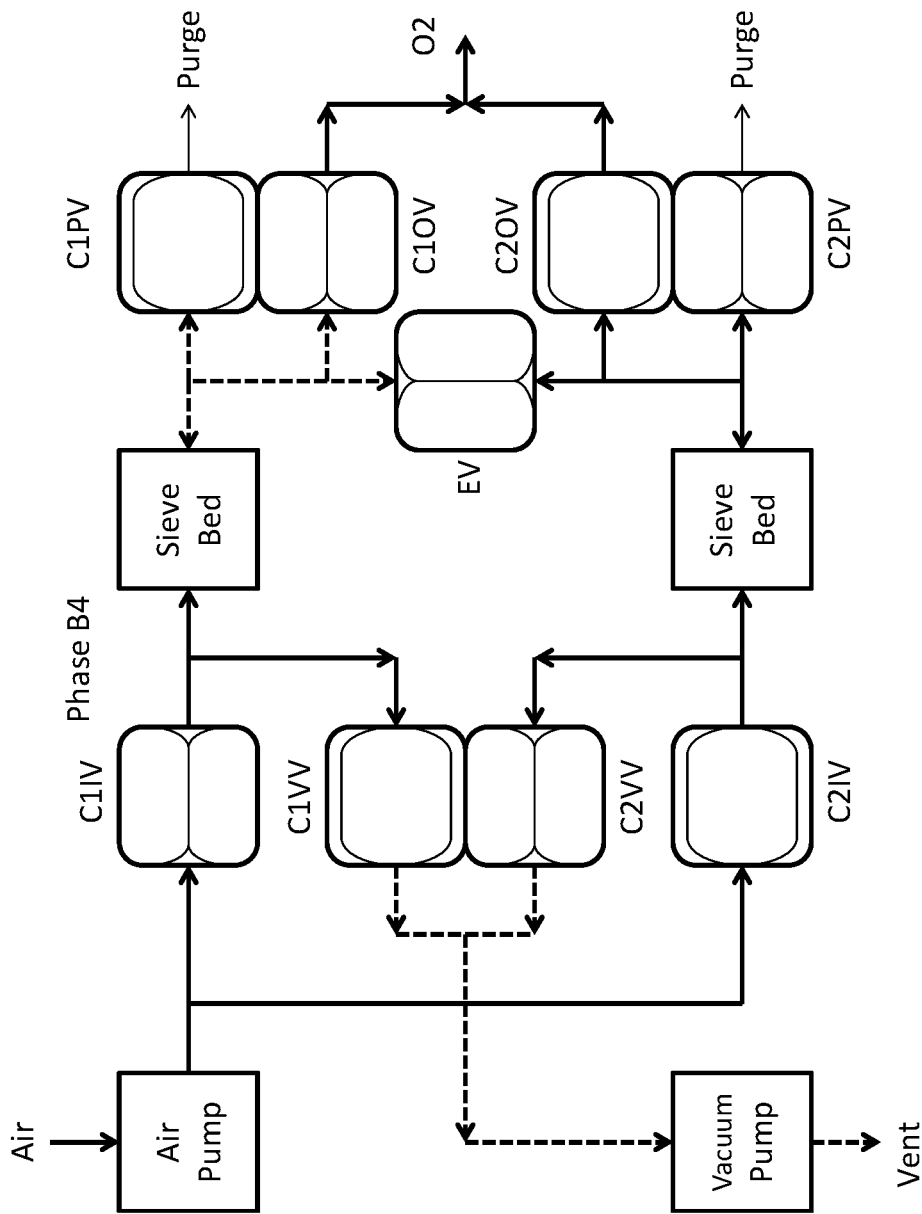

Operation State B4 (FIG. 4H)

| Operation: | Separation | Status: | Description: |
|---|---|---|---|
| Phase: | B | | |
| State: | B4 | | |
| Air Pump | AP | on | Compressing air to operating pressure into a sieve bed for separation |
| Vacuum Pump | VP | on | Evacuating air to negative operating pressure from a sieve bed for regeneration |
| Purge Reservoir | PR | inactive | Used to set the pressure in a sieve bed to ambient - saves energy |
| O2 Reservoir | OR | inactive | Used to hold produced O2 and to lower the pressure to near ambient |
| Equalization Valve | EV | closed | Used to pre-pressurize the next sieve bed separation phase - saves energy |
| Channel: | 1 | | |
| Sieve Bed | C1SB | de-pressurizing | Sized for ½ of total required O2 production |
| Input Valve | C1IV | closed | Passes compressed air into sieve bed |
| Purge Valve | C1PV | open-function 2 | Function 1: releases diluted O2 before O2 harvest: to Purge Reservoir |
| | | | Function 2: returns next sieve bed separation phase to ambient: from Purge Reservoir |
| Output Valve | C1OV | closed | Passes generated O2 to O2 Reservoir |
| Vent Valve | C1VV | open | Passes pressure from sieve bed to vacuum pump |
| Channel: | 2 | | |
| Sieve Bed | C2SB | pressurizing> | Sized for ½ of total required O2 production |
| Input Valve | C2IV | open | Passes compressed air into sieve bed |
| Purge Valve | C2PV | closed | Function 1: releases diluted O2 before O2 harvest: to Purge Reservoir |
| | | | Function 2: returns next sieve bed separation phase to ambient: from Purge Reservoir |
| Output Valve | C2OV | open | Passes generated O2 to O2 Reservoir |
| Vent Valve | C2VV | closed | Passes pressure from sieve bed to vacuum pump |

Figure 5:
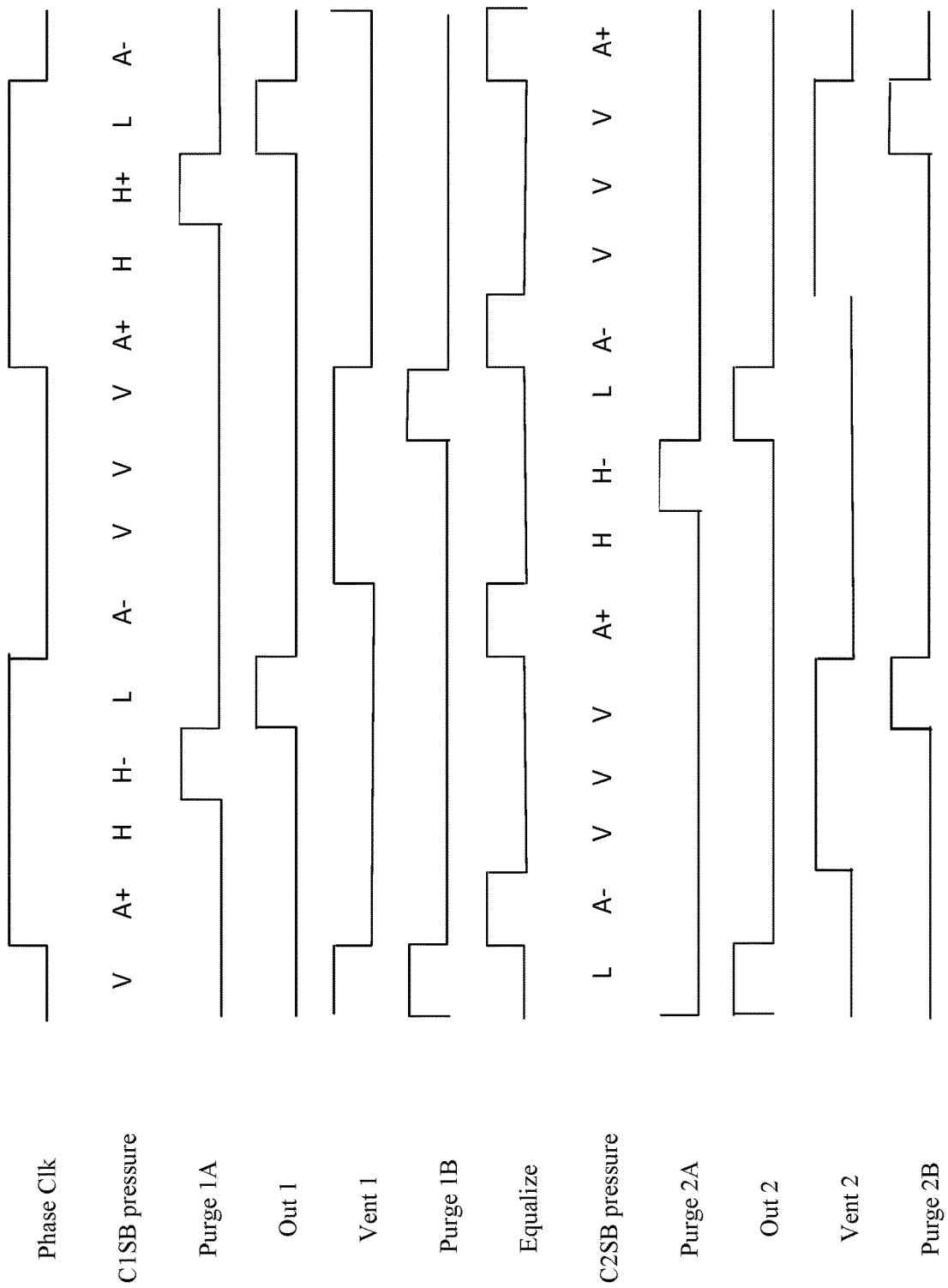
FIG. 5 is a timing diagram for the microelectromechanical gas concentrator system of FIG. 4 with purge feedback.

Referring now to FIG. 5, a timing diagram for the gas concentrator 40 operating according to a rapid vacuum pressure swing adsorption (RVPSA) principle and including the purge reservoir 42b is shown. This timing arrangement includes signals (purge 1A and purge 1B) that are used to open the purge valves C1PV, 34a and C2PV 34b (FIG. 4A) at an end of a previous cycle. The basic operation is similar to that of FIG. 3 (without the purge reservoir) except that the gas concentrator 40 includes the purge reservoir 42b (implemented as a bladder, a flexible storage element) that has two functions. One function of the purge reservoir 42b is to store purged gases from the gas concentrator 40 that can be recycled back to the input micro pump 14 (either directly or through the filter 12) and the other function is to minimize the amount of gas the input pump 14 needs to pump through the sieve beds 25a, 25b once one of the sieve beds 25a, 25b is fully vented by returning the pressure in that sieve bed from vacuum to ambient.

Recall, that with the processing of FIG. 1-3, the input micro pump 14 pressurizes the sieve bed of a given channel to about 7 psig, while the vacuum pump 16 vents the other channel in a given phase. Thus, at the end of a phase, the vented sieve bed and channel are at about −7 psig relative to ambient. Thus, on the next cycle the micro pump 14 would need to pressurize the sieve bed to +7 psig or a total net difference of 14 psig. By using purge function 2 to return the fully vented sieve bed to ambient pressure, just prior to the start of a new cycle, that allows the input micro pump 14 to pump into a 0 psig channel rather that −7 psig channel which uses less energy and is more efficient. The collapsible purge reservoir 42b would have a volume necessary to return the fully vented sieve bed to ambient pressure.

Valves

In some implementations, the valves are miniature solenoid activated valves. In other implementations the valves can be adaptions of sliding or flap valves discussed in the co-pending applications. In still other implementations, the valves are membrane based valves, as now discussed.

Figure 6A:
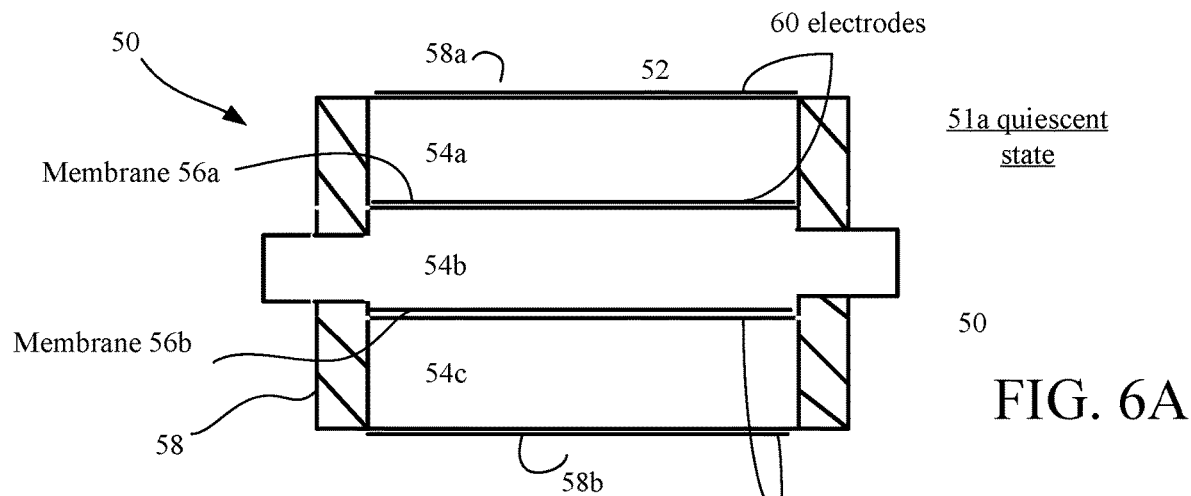
FIGS. 6A-E are cross-sectional views of membrane based valves for the gas concentrator system of FIGS. 1-4H.
Figure 6B:
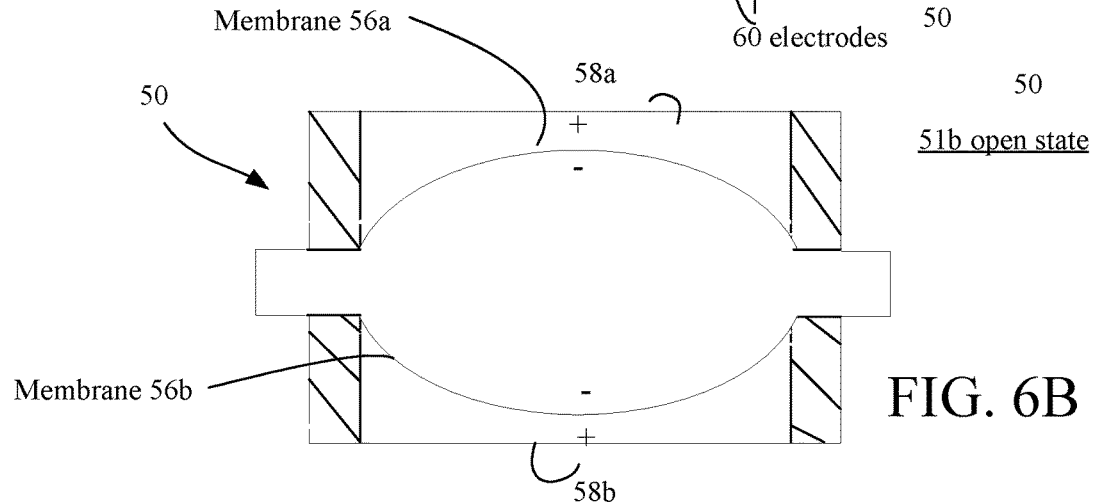
Figure 6C:
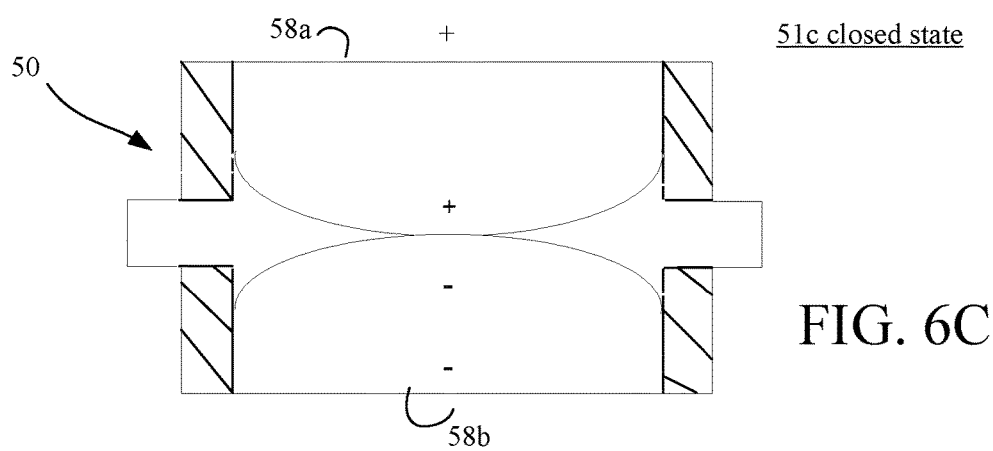

Referring now to FIGS. 6A-6C, three states of a membrane valve 50 are shown. FIG. 6A shows a quiescent state 51a (partially opened valve state), FIG. 6B shows a fully open operational state 51b, while FIG. 6C shows a fully closed operational state 51c. The valve 50 has a chamber 52 that is divided into three compartments 54a-54c by a pair of membranes 56a, 56b anchored to a valve body 58 having, e.g., 6 walls to form a geometric solid, two of the walls 58a, 58b being referenced. In this implementation, a middle one of the compartments 54b has a pair of ports (not referenced). The valve 50 closes when the membranes move towards each other, pinching off the middle compartment 54b, thus isolating the ports at opposite ends of the compartment 54b. When the membranes 56a, 56b move away from each other the valve 50 is open and couples the ports at the opposite ends of the compartment 54b. The membranes 56a, 56b move in two opposite directions about a central, nominal location when not actuated.

Actuation of the membranes is by electrostatic force. Electrodes 60 are attached to one of the major surfaces of each of the fixed end walls 58a, 58b and to one of the major surfaces of each of the membranes 56a, 56b. These electrodes are electrically isolated from each other and are fed electrical signals such as those in the timing diagrams of FIGS. 3 and 5, according to which of the valves a given membrane valve is being used for.

Referring to FIG. 6B, during an valve opening operation when two adjacent electrodes both have positive charge or both have negative charge (as shown) that will cause the membranes 56a, 56b disposed between the walls 58a, 58b to repel each other. Also when the walls 58a, 58b have opposite charge on respective adjacent electrodes that will cause the repelling membranes 56a, 56b to be attracted to walls 58a, 58b adjacent to the corresponding membranes, further increasing the mutual repulsion of the membranes 56a, 56b and thus opening the valve 50.

Referring to FIG. 6C, during a valve closing operation when two adjacent electrodes both have opposite charge one positive charge the other negative charge (as shown) that will cause the membranes 56a, 56b disposed between the walls 58a, 58b to be attracted to each other. Also when the walls 58a, 58b have like charge as the charge on respective electrodes adjacent to the walls that will repel the membranes 56a, 56b from the walls 58a, 58b thus further attracting the membranes 56a, 56b to each other and thus closing the valve 50.

The two electrodes with dielectric form a parallel plate electrostatic actuator. The electrodes generally have small sizes and low static power consumption (very low current). A high voltage can be applied to each electrode to actuate the compartment, but the actuation is performed at a very low current.

Figure 6D:
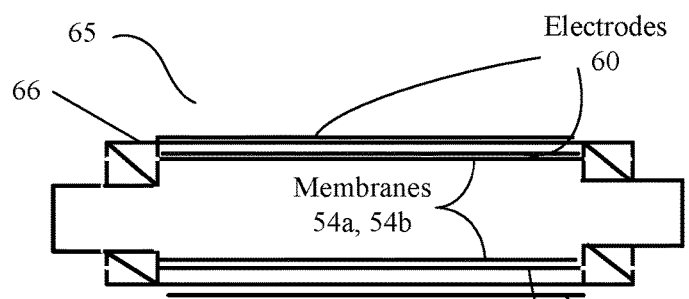

As shown in FIG. 6D, in some implementations a valve 65 has a single compartment. The electrodes 60 on the end caps of the body are dielectrically isolated (e.g., by a portion of the valve body 66 from electrodes 60 on the membranes 54a, 54b.

Figure 6E:
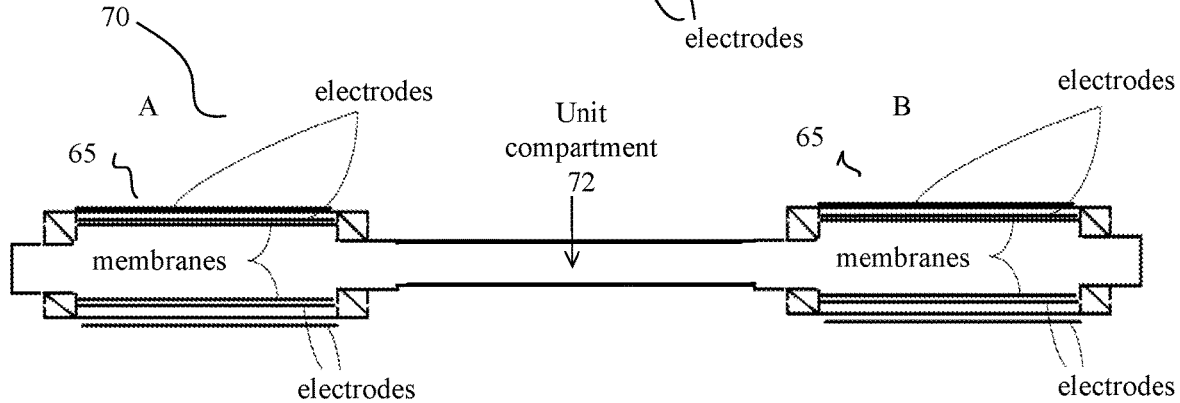

Referring now to FIG. 6E, in some implementations of the gas concentrator 10, a two stage valve 70 is used to release a unit volume of gas. The two stage valve 70 uses a unit compartment 72 (to expel a unit amount of fluid). The unit compartment 72 has a pair of ports at which two single compartment valves 65 (FIG. 6D) are coupled, as shown. The unit compartment 72 is disposed between the two single compartment valves 65. The unit compartment 72 is used to capture a unit (i.e., defined volume of fluid, e.g., gas). This valve 70 can be used as C1PV and C2PV valves (34a, 34b FIG. 2A, etc.) to purge a unit volume amount of gas from the gas concentrator 50 prior to harvesting of purged gas from the purge reservoir (FIG. 4) to return sieve beds 25a, 25b to ambient at the start of a new cycle.

An operational Sequence to Purge a Unit Volume is as follows:

1. Start cycle by opening valve A with valve B closed to allow gas to enter through valve A and into the unit purge volume (unit compartment) 72.
2. Equilibrate pressure on both sides of Valve A.
3. Close Valve A.
4. Open Valve B to allow gas in the unit purge volume (unit compartment) 72 to enter valve B and flow out of the two stage valve.
5. Close Valve B to end cycle.

Referring again to FIGS. 3 and 5, during each phase cycle, the valves in the valve assembly 18, e.g., FIG. 2A, are activated according to the timing of the appropriate one of these figures (of course it is understood that alternative timing and/or dynamically modified timing can be used). For membrane based valves, the valves are activated such that the compartment of each valve is opened by the membranes being repulsed from each other to open the valve, or closed by membranes being attracted to each other.

To close a valve, voltages of opposite polarities are applied to the electrodes on opposing walls of these compartments building up positive and/or negative charge. Voltages (charge) of opposite signs cause the two membranes to attract each other to close off a channel, and the voltages of the same polarity cause the two membranes to repel each other. The fixed walls do not move. The membranes move towards a direction of the attraction force or a direction of the repelling force.

The material of the membranes and voltages applied to the membranes and the end walls are chosen such that when activated, each membrane expands substantially half the distance d between the nominal positions of adjacent membranes and continues to expand to seal off the channel but not to exceed either the dielectric breakdown voltage or elastic limits of the membranes. In the end compartments where the distance between the nominal position of the membrane and the fixed wall can be either d or d/2, the activated membrane reduces the volume of the compartment to close to d/2 or zero respectively, (in an opening operation increasing flow rate through the compartment). For the intermediate compartment, by moving each membrane by d/2, a volume of a compartment is expanded to close to $2*V_i$ in an opening operation and reduced to close to zero in a closing operation.

In some implementations, four types of electrical signals are used to drive the membranes. The four types are:

V−: a DC reference for all the voltages; may be used to drive some membranes directly;

V+: a DC high voltage used to drive some membranes directly and switched for others;

V1: a periodic AC waveform used to drive some membranes to control operation. It includes a 50% duty cycle and swings between V− and V+ in one full pumping cycle.

V2: identical to V1 except it is 180 degrees out of phase.

Sets of waveforms are applied onto the four electrodes on the fixed walls and the membranes and which are derived from the timing signals in FIGS. 3 and/or 5.

Figure 7:
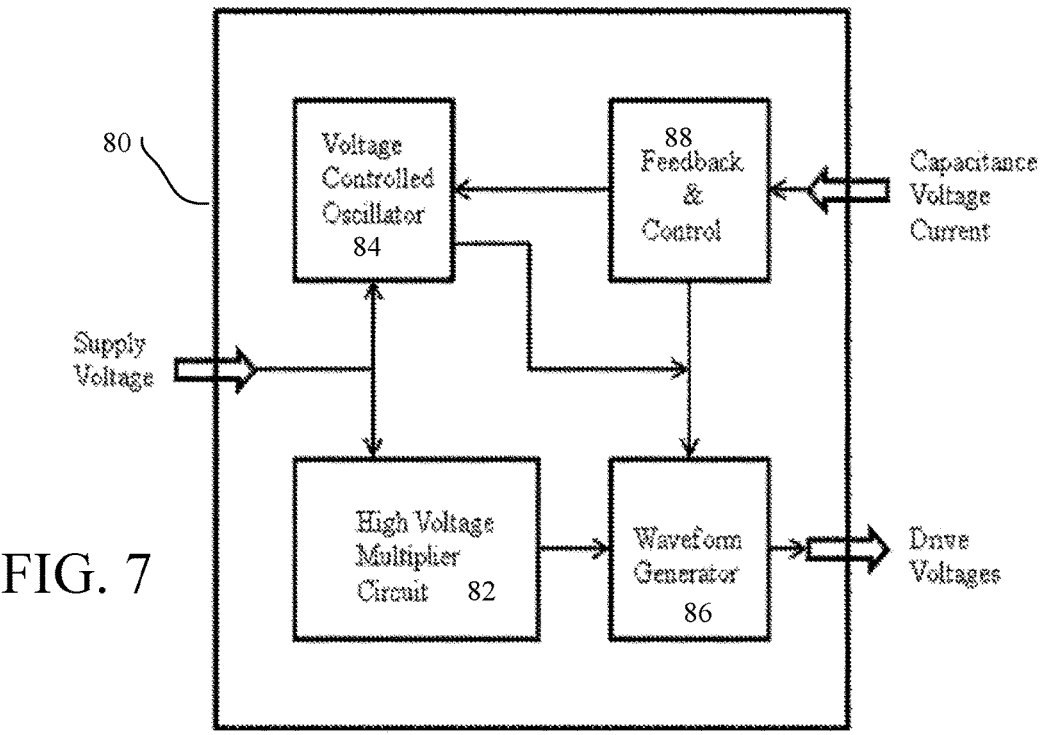
FIG. 7 is a block diagram of circuitry for the microelectromechanical gas concentrator system.

Referring now to FIG. 7, an example of drive circuitry 80 for applying voltages to the valves is shown. The drive circuitry 80 receives a supply voltage, (and in some implementations sensor signals from the implementation of FIG. 2) and outputs drive voltages to the valves. The drive voltages would depend on the type of valves employed in the gas concentrator. For membrane based valves the arrangement discussed above could be used.

The drive circuitry 80 includes a high voltage multiplier circuit 82, a voltage controlled oscillator ("VCO") 84, a waveform generator circuit 86, and optionally a feedback and control circuit 88. The high voltage multiplier circuit 82 multiplies the supply voltage up to a desired high voltage value, e.g., about 100V to 700V, nominally, 500 V. Other voltages depending on material characteristics, such as dielectric constants, thicknesses, mechanical modulus characteristics, electrode spacing, etc. can be used. In some implementations, the high voltage multiplier circuit 82 includes a voltage step-up circuit (not shown). The voltage controlled oscillator 84 produces a drive frequency for the valve signals. The oscillator 84 is voltage controlled and the frequency can be changed by an external control signal so that the valves push more or less gas based on flow rate requirements. The waveform generator circuit 86 generates the drive voltages for the electrodes on the membranes. As described previously, some of the drive voltages are AC voltages with a specific phase relationship to each other. The waveform generator circuit 86 controls these phases as well as the shape of the waveforms. The feedback and control circuit 88 receives signals that provide measures of capacitance, voltage and/or current and the circuit 88 can produce a feedback signal to provide additional control of the waveform generator 86 of the circuit to help adjust the drive voltages for desired performance. Such signals can measure pressure, flow, and concentration, etc. The drive circuit 80 can be separate from or part of the drive circuit (not shown) used with the micro pumps 14, 16.

As with the micro pumps described in the above applications, the features of the membrane valves 50, 65, 70 can have a distance between the membranes in their nominal positions of about 50 microns, and the nominal volume $V_i$ can range from nanoliters to microliters to milliliters, e.g., 0.1 microliters. In some implementations, the end compartments each has a nominal volume $V_e$ that is half the nominal volume of the intermediate compartment, e.g., about 25 microns. The compartments can have different sizes. The sizes are chosen based on, e.g., specific process requirements of a roll to roll manufacturing line, as well as, power consumption, and application considerations. Other details can be adapted from those mentioned for micro pumps as set forth in the above mention incorporated by reference published patent applications.

Figure 8:
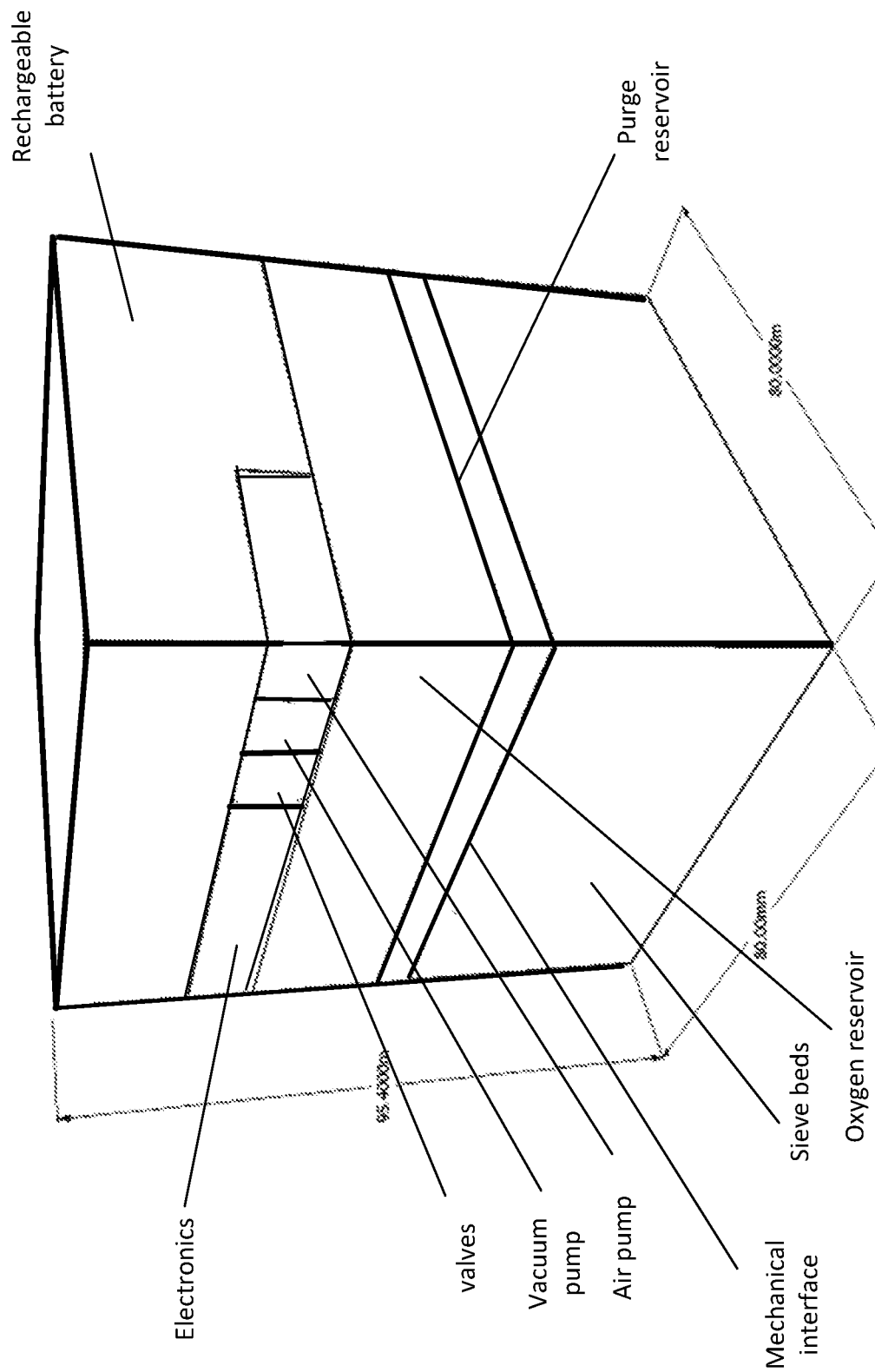
FIG. 8 is conceptual view of a microelectromechanical gas concentrator system for volumetric considerations.

Referring now to FIG. 8 an example conceptual volumetric view of the gas concentrator is shown. This view depicts typical relative volumes envisioned for various components of the gas concentrator. Conceptually an example of the size could be 95.4 mm×80 mm×80 mm or about 0.61 liters. The weight could be less than a pound. The sieve beds are shown internal, but could be external and the mechanical interface includes ports to the sieve bed. The electronics include circuitry to monitor, control and a user interface (display controls). The view also shows conceptually the VP vacuum pump, VS valve switches, AP air pump and a rechargeable battery that is expected to consume a large proportion of the volume. A recharge interface would also be included as part of the battery space utilized.

In conventional designs, the sieve beds are generally among the largest components and are designed to produce required flow rates at required concentrations. For a given output requirement, the size of the sieve beds can be reduce by utilizing active separation and regeneration processes, pressure and vacuum pumps. Higher pressure/vacuum can also help reduce sieve bed size but at a cost of stored energy in the battery and reduces "run time." Electrostatic drive is the most efficient and will help reduce the size of the battery for a given run time. Sieve bed geometry can take advantage of a layered approach offered by the R2R MEMS technology to decrease mass transport limitations and improve gas separation capacity.

Size is an advantage that would be provided by the disclosed gas concentrator 10. If the sieve beds 25a, 25b are implemented into the R2R MEMS device, the battery might be the largest external device, as shown in FIG. 8. Weight is another advantage followed by run time. Cost is also a significant advantage, and could allow more people to afford its use. A typical conventional unit generally can be about 5-6 liters in volume, 4-10 lbs in weight and run for 5-6 hrs. Typical characteristics for the gas concentrator 10 are 0.5 or less liters in volume, about a pound in weight and about 5-6 hrs. run time at a cost much less expensive by at least an order of magnitude than the typical conventional unit.

Below are some example criteria for choosing the materials of the different parts of the membrane valve.

Valve body—The material used for the body of a membrane valve may be defined by the requirements of the application, for instance, if the valves are made of the same material as the micro pumps. The material needs to be strong or stiff enough to hold its shape to provide the chamber volume. The material is electrically non-conductive.

Membrane—The material for this part forms a tympanic structure (a thin membrane covering the compartments). As such, the material is required to bend or stretch back and forth over a desired distance and has elastic characteristics. The membrane material is impermeable to fluids, including gas and liquids, is electrically non-conductive, and possesses a high breakdown voltage. Examples of suitable materials include silicon nitride and Teflon and PET.

Electrodes—These structures are very thin and comprised of material that is electrically conductive. Because the electrodes do not conduct much current, the material can have a relatively high electrical resistance, although the high resistance feature is not necessarily desirable. The electrodes are subject to bending and stretching with the membranes, and therefore, it is desirable that the material is supple to handle the bending and stretching without fatigue and failure. In addition, the electrode material and the membrane material will need to adhere well to each other, e.g., will not delaminate from each other, under the conditions of operation. Examples of suitable materials include gold, aluminum, and platinum.

Electrical interconnects—The drive voltage is conducted to the electrode on each membrane of each compartment. Electrically conducting paths to these electrodes can be built using conductive materials, e.g., gold, aluminum, and platinum.

Roll to Roll Processing for Producing Gas Concentrators

Roll to roll processing line can comprises several stations, e.g., station 1 to station n (not shown) and which can be or include enclosed chambers) at which deposition, patterning, and other processing occurs. Processing viewed at a high level thus can be additive (adding material exactly where wanted) or subtractive (adding material and removing material in places where wanted). Deposition processing includes evaporation, sputtering, and/or chemical vapor deposition (CVD), as needed, as well as printing. The patterning processing can include depending on requirements techniques such as scanning laser and electron beam pattern generation, machining, optical lithography, gravure and flexographic (offset) printing depending on resolution of features being patterned. Ink jet printing and screen printing can be used to put down functional materials such as conductors. Other techniques such as imprinting and embossing can be used.

The original raw material roll is of a web of flexible material. In roll to roll processing the web of flexible material can be any such material and is typically glass or a plastic or a stainless steel. While any of these materials (or others) could be used, plastic has the advantage of lower cost considerations over glass and stainless steel and is a biocompatible material for production of the gas concentrator.

In manufacturing sacrificial filling material that can be employed is, e.g., polyvinyl alcohol (PVA). The sacrificial filling material can be used, if needed, to support the membrane over the body during processing. Solvents then would be used in the manufacturing process to subsequently remove this sacrificial filling material.

The roll having the valve units (membrane valves and paths connections to the membrane valves, with electrode and electrical connections) are diced and collected and can either be fabricated along with the micro pumps or can be assembled subsequent to fabrication of the micro-pumps and packaged together. That is depending upon the layout of the micro pump units on the web it may be possible to integrate the micro pump with the valve units on the same web.

Membrane valves can be constructed individually or as a valve assembly with interconnection channels, as generally shown in FIGS. 1-4.

Consider FIG. 9 as an illustrative mask for valve assembly 18. The valve assembly 18 can be constructed as a unitary unit or as two units. For the valve type 50 discussed in FIGS. 6A-6C, a stack of three body layers spaced by two membranes with four electrodes on two walls of the stacked body layers and the other two electrodes on one of the major surfaces of each of the membranes. Conduits (illustrated by lines in FIG. 9 not referenced) could be machined from the body layers much like cavities that provide the membrane spaced compartments are machined from the body layers, using any of the techniques discussed in the above incorporated by reference applications. As for the membrane valves 65, 70, processing to produce those types of valves would be similar but involve a single body layer and two membranes and can be adapted from the construction principles used for the micro pumps according to any of the processes discussed in the above applications, as in some aspects the membrane valves 65, 70 are a single, actuated intermediate chamber of a micro pump, taking into consideration features as discussed herein.

The sieve beds 25a, 25b of the zeolites can be constructed on different webs and these can be wedded together with micro pumps, etc. The construction of the micro pumps can be according to any of the processes discussed in the above incorporated by reference applications.

A sheet of a flexible material such as a glass or a plastic or a stainless steel is used as a web. For the particular implementation the material is a plastic sheet, e.g., Polyethylene terephthalate (PET).

The sheet is a 50 micron thick sheet. Other thicknesses could be used (e.g., the sheet could have a thickness between, e.g., 25 microns and 250 microns (or greater). The thicknesses are predicted on desired properties of the microelectromechanical system to be constructed and the handling capabilities of roll to roll processing lines. These considerations will provide a practical limitation on the maximum thickness. Similarly, the minimum thicknesses are predicted on the desired properties of the microelectromechanical system to be constructed and the ability to handle very thin sheets in roll to roll processing lines.

For the membrane valves, the layers would have thicknesses as mentioned above approximately 50 microns for the body and 5 microns for the membrane elements. However, other thicknesses are possible. A metal layer, e.g., 50 to 150 Angstroms for the electrodes is provided by various approaches, such as evaporation or other techniques. Such metallized films are also commercially available.

The sheet from a roll is patterned at an ablation station, e.g., a laser ablation station 1. A mask (not shown) is used to configure the laser ablation station to remove or to define or form a compartment, as well as alignment holes (not shown but discussed in the published applications). Vias are also provided for electrical connections, as shown and discussed in the published application. The micro-machining ablates away the plastic to form the compartment of the valve while leaving the frame portion.

The sheet with the compartment is laminated at a lamination station to a sheet, e.g., 5 micron thick sheet of PET, with a metallic layer of Al of 100 A on a top surface of the sheet. This sheet forms the membranes and electrodes over a compartment. This could be the intermediate compartment and thus have ports defined in the frame. End caps can be formed on second and third webs. The sheets are machined to provide the alignment holes (not shown) prior to or subsequent to coating of the metallic layer.

End cap units and intermediate units are then stacked to form individual valves or if passages are also produced interconnected individual valves to provide the valve assembly. A jig as discussed in the co-pending published application that comprises vertical four posts mounted to a horizontal base can be used to stack individual ones of cut dies (of valves or valve assemblies). On the jig an end cap (e.g., a 50 micron PET sheet with a metal layer) is provided and over the end cap an intermediate unit is provided. The intermediate unit is spot welded (applying a localized heating source) to hold the unit in place on the jig. A second top endcap is provided on the stacked intermediate unit and spot welded. Once a stack is completed, with the top cap, the stack unit is sent to a lamination station, where the stack is laminated, laminating the unit and caps together. The end cap and top cap can be part of the packaging as well. Otherwise sets of repeatable units can be laminated in pairs. Other stacking techniques for assembly are possible with or without the alignment holes.

In summary, the gas concentrator 50 will have the micro pumps (acting as micro-blowers) internal to the gas concentrator 50 and used for both the air pump and vacuum pump. The active valves 18 will be internal membrane type valves as shown. The valve types discussed in FIGS. 6A-6C and 6D can be used for all of valves in the various valve assemblies. In some instances, the valve in FIG. 6E could be used in lieu of the valve types of FIGS. 6A-6D.

In some instances a peristaltic micro pump approach could be used. One peristaltic pump concept is discussed in Application Ser. No. 62/470,460 filed Mar. 13, 2017 entitled "Micro Pump Systems and Processing Techniques" the entire contents of which are incorporated herein by reference. In this approach, three micro pump elements are in a series configuration. The micro pump elements do not have fixed valves and instead a first and third ones of the micro pump elements act as valves for the second micro pump element that is intermediate the first and third micro pump elements.

The sieve beds 25a, 25b can be internal or external and may have material coated channels. The pressure equalizing reservoir can be internal or external, such as an external balloon type structure. The internal channels are defined during micro fabrication process and electrical connections that are internal are defined during micro fabrication process.

The electronics 22 can be external—miniaturized circuits that will implement the phase timing via a software algorithm, monitoring of internal integrated sensors for pressure, flow, concentration, etc. and well as control of the internal or external switches, pumps, and a display, etc. The electronics 22 can be built-in. The electronics 22 can be implemented as any one of a variety of different electrical or electronic control, computing or processing devices, and can perform any combination of the various functions discussed above to control various components of the disclosed gas concentrator, e.g., valves, pumps, etc.

The electronics 22 can be implemented as a controller that generally, and optionally, includes any one or more of a processor (or multiple processors), a memory, a storage device, and input/output device. Some or all of these components can be interconnected using a system bus. The processor is capable of processing instructions for execution. In some embodiments, the processor is a single-threaded processor or a multi-threaded processor or a hardware controller capable of processing instructions stored in memory or on the storage device. Some implementations can include a display device and the control is configured to display information for a user and to execute various monitoring and control functions discussed above. Suitable processors for the systems disclosed herein include both general and special purpose microprocessors.

The memory stores information within the system, and can be a computer-readable medium, such as a volatile or non-volatile memory. The storage device can be capable of providing mass storage. In general, the storage device can include any non-transitory tangible media configured to store computer readable instructions. Storage devices include all forms of non-volatile memory including by way of example, semiconductor memory devices, such as EPROM, EEPROM, and flash memory devices, etc. Processors and memory units disclosed herein can be supplemented by, or incorporated in, or provided from ASICs (application-specific integrated circuits) and the like.

The features described herein, including components for performing various measurement, monitoring, control, and communication functions, can be implemented in digital electronic circuitry, or in computer hardware, firmware, or in combinations of them. Methods steps can be implemented in a computer program product tangibly embodied in an information carrier, e.g., in a machine-readable storage device, for execution by a programmable processor, and features can be performed by a programmable processor executing such a program of instructions to perform any of the steps and functions described above. Computer programs suitable for execution by one or more system processors include a set of instructions that can be used directly or indirectly, to cause a processor or other computing device executing the instructions to perform certain activities, including the various steps discussed above.

Elements of different implementations described herein may be combined to form other embodiments not specifically set forth above. Elements may be left out of the structures described herein without adversely affecting their operation. Furthermore, various separate elements may be combined into one or more individual elements to perform the functions described herein and algorithms that provide different time of valves or different vales could be used to affect concentrator operation. Other embodiments are within the scope of the following claims. For example, in some implementations only one micro pump could be used. This arrangement would include a multiplexer valve that multiplexes gas from the micro pump to deliver gas to the first channel 10a on a first portion of a cycle and a draws gas from the first channel 10a on a second portion of the cycle.

What is claimed is:

1. A gas concentrator, comprises:
    a micro pump having a micro pump inlet and a micro pump outlet;
    a sieve bed having a first port and a second port; and
    a valve assembly for controlling entry of a multi-component gas from the micro pump outlet into the first port of the sieve bed, venting of a first component of the multi-component gas, and feeding a concentrated second component of the multi-component gas from the second port of the sieve bed to an outlet port of the gas concentrator, and with the valve assembly being of a unitary construction, and the valve assembly comprising:
    a plurality of valves, with at least some of the plurality of valves being membrane valves that include:
        a body having a chamber with first and second ports through the chamber and the body that define a passage through the body; and
        a pair of spaced membranes each carrying an electrode, the pair of spaced membranes affixed to walls of the body and disposed in the chamber, with the pair of spaced membranes configured upon application of charges to the electrodes to attract to each other to close the passage through the chamber in a first mode and to repel each other to open the passage through the chamber in a second mode.

2. The gas concentrator of claim 1 wherein the plurality of valves are disposed on a common substrate layer, with the plural valves interconnected among inlets and outlets of the plural valves, via passages disposed in the common substrate layer.

3. The gas concentrator of claim 1 wherein the micro pump, the sieve bed and the valve assembly provide a first channel, the sieve bed is a first sieve bed, and the gas concentrator further comprises:
a second channel comprising:
a second sieve bed having an input coupled via the valve assembly to the micro pump, and the second sieve bed having a second port; and
an equalization valve coupled between the second ports of the first and second sieve beds.

4. The gas concentrator of claim 1 wherein the plurality of valves include:
an input valve having an input port coupled to the micro pump outlet and having an output port coupled to the first port of the sieve bed, with the input valve controlled by an input signal to selectively open and close the input valve;
a purge valve having an input port coupled to the second port of the sieve bed, and having an outlet port coupled to a purge line of the gas concentrator, with the purge valve controlled by a purge signal to selectively open and close the purge valve;
a vent valve having an input port coupled to the first port of the sieve bed and having an output coupled to a vent output of the gas concentrator, the vent valve controlled by a vent signal to selectively open and close the vent valve; and
an output valve having an input port coupled to the second port of the sieve bed and having an output port coupled to the output of the gas concentrator, the output valve controlled by an output signal to selectively open and close the output valve.

5. The gas concentrator of claim 4 wherein the micro pump, the sieve bed and the plurality of valves of the valve assembly provide a first channel, and the gas concentrator further comprises:
a second channel comprising:
a second sieve bed coupled to the valve assembly.

6. The gas concentrator of claim 5 wherein the input, purge, vent and output valves and signals are first valves and first signals, and the valve assembly further comprises for the second channel, a second plurality of valves comprising:
a second input valve having an input port coupled to the micro pump outlet and having an output port coupled to a first port of the second sieve bed, with the second input valve controlled by a complement of the first signal to selectively open and close the second input valve;
a second purge valve having an input port coupled to a second port of the sieve bed, and having an outlet port coupled to the purge line of the gas concentrator, with the second purge valve controlled by a second purge signal to selectively open and close the second purge valve;
a second vent valve having an input port coupled to the first port of the sieve bed and having an output coupled to the vent output of the gas concentrator, the second vent valve controlled by a second vent signal to selectively open and close the vent valve;
an equalization valve coupled between the second ports of the first and second sieve beds; and
an output valve having an input port coupled to the second port of the second sieve bed and having an output port coupled to the output of the gas concentrator, the output valve controlled by a second output signal to selectively open and close the output valve.

7. The gas concentrator of claim 1 wherein the micro pump is a first micro pump and the sieve bed is a first sieve bed, with the gas concentrator further comprising:
a second sieve bed having a first port coupled to the valve assembly; and
a second micro pump coupled to a vent port of the valve assembly.

8. The gas concentrator of claim 7 wherein the first and second sieve beds have second ports and the valve assembly further comprises:
an equalization valve coupled between the second ports of the first and second sieve beds.

9. The gas concentrator of claim 1 further comprising:
an output gas reservoir coupled to an output of the valve assembly.

10. The gas concentrator of claim 1 wherein the valve assembly is further configured to purge gas from the sieve bed and the gas concentrator further comprises:
a purge gas reservoir coupled to a purge output port of the valve assembly.

11. The gas concentrator of claim 1 further comprising:
electronic circuitry including timing generator circuitry having output signal lines coupled to electrodes on the valves to provide timing signals to valves in the valve assembly.

12. The gas concentrator of claim 11 wherein the electronic circuitry further includes a waveform generator that produces the signals having either a positive charge or a negative charge relative to a ground potential.

13. A gas concentrator, comprises:
a micro pump;
a sieve bed having a first port and a second port; and
a valve assembly for controlling entry of a multi-component gas from the micro pump into the first port to the sieve bed, venting of a first component of the gas, and feeding a concentrated second component of the gas from the second port of the sieve bed to an outlet port of the gas concentrator, wherein the valve assembly, comprises a plurality of valves, each of the plurality of valves including:
a body having a chamber with first and second ports through the body that define a passage through the body; and
a pair of spaced membranes each carrying an electrode, the pair of spaced membranes affixed to walls of the body and disposed in the chamber, with the pair of spaced membranes configured upon application of charges to the electrodes to attract to each other to close the passage through the chamber in a first mode and to repel each other to open the passage through the chamber in a second mode.

14. The gas concentrator of claim 13, wherein the valve assembly further comprises:
a first end cap compartment; and
a second end cap compartment, with the first end cap compartment disposed over a first surface of the valve assembly and the second end cap compartment disposed over a second surface of the valve assembly.

15. The gas concentrator of claim 13, further comprises:
electronic circuitry including timing generator circuitry having output signal lines coupled to electrodes to control operation of the valve assembly.

16. The gas concentrator of claim 13 wherein the valve assembly is a first valve assembly and the body and the plurality of pairs of spaced membranes are a first body and a first plurality of pairs of spaced membranes, with the valve assembly further comprising:

a second valve assembly, comprising:

a second body having a chamber with first and second ports through the second body that define a passage through the second body; and a second plurality of pairs of spaced membranes each carrying an electrode, the second plurality of pairs of spaced membranes affixed to walls of the body and disposed in the chamber of the second body, with the second plurality of pairs of spaced membranes configured upon application of charges to the electrodes to attract to each other to close the passage through the chamber in a first mode and to repel each other to open the passage through the chamber in a second mode.

17. The valve of claim 16 further comprising:

electronic circuity including timing generator circuity having output signal lines coupled to electrodes to control operation of the first valve assembly and second valve assembly.

18. The gas concentrator of claim 13 wherein at least one of the plurality of valves in the valve assembly includes a first valve element, a second valve element, and a unit compartment that is coupled in series in between an output of the first valve element and an input of the second valve element.

19. The gas concentrator of claim 18 further comprising:

electronic circuity including a timing generator circuity having output signal lines coupled to control operation of the first valve element and the second valve element, according to a sequence that:

opens the first valve element while the second valve element is closed to allow gas to enter through the first valve element and into the unit compartment;

equilibrates gas pressure in the first valve element and unit compartment;

closes the first valve element; and opens the second valve element to allow gas in the unit compartment to enter the second valve element and flow out of the second valve element.

20. The gas concentrator of claim 1 wherein the micro pump further includes a sensor to provide a sensor signal that is a measure of one or more of pressures, flows, gas concentrations, and temperatures.

21. The gas concentrator of claim 1 further comprising:

a sensor that provides a sensor signal that is a measure of one or more of pressures, flows, gas concentrations, and temperatures of gas that is vented from the valve assembly; and a second micro pump having an inlet that receives the gas vented from the valve assembly and having an outlet that vents the received, vented gas.

22. The gas concentrator of claim 5 further comprising:

a sensor that provides a sensor signal that is a measure of one or more of pressures, flows, gas concentrations, and temperatures of gas that is vented from the valve assembly; and a second micro pump having an inlet that receives the gas vented from the valve assembly and having an outlet that vents the received, vented gas.

23. The gas concentrator of claim 20 wherein the valve assembly has three paths, with a first path being a gas separation path that takes air from first micro pump and delivers a concentrated stream of the gas to a reservoir, a second path is a vent path that vents vented gas from the sieve bed, and a third path being is an equalization path.

24. The gas concentrator of claim 23 wherein the equalization path pre-pressurizes a next one of the first and second sieve beds to receive concentrated gas.

25. The gas concentrator of claim 1 wherein the gas concentrator is an oxygen concentrator that concentrates oxygen and vents nitrogen.

* * * * *